US011116397B2

(12) United States Patent
Quinn et al.

(10) Patent No.: US 11,116,397 B2
(45) Date of Patent: Sep. 14, 2021

(54) METHOD AND APPARATUS FOR MANAGING SENSORS

(71) Applicant: WELCH ALLYN, INC., Skaneateles Falls, NY (US)

(72) Inventors: David E. Quinn, Skaneateles Falls, NY (US); Craig M. Meyerson, Skaneateles Falls, NY (US); John A. Lane, Skaneateles Falls, NY (US); Kenzi L. Mudge, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 892 days.

(21) Appl. No.: 14/798,798

(22) Filed: Jul. 14, 2015

(65) Prior Publication Data

US 2017/0014085 A1 Jan. 19, 2017

(51) Int. Cl.
*G16H 40/67* (2018.01)
*A61B 5/00* (2006.01)
*A61B 5/0205* (2006.01)
*A61B 5/024* (2006.01)
*A61B 5/08* (2006.01)
(Continued)

(52) U.S. Cl.
CPC .......... *A61B 5/0002* (2013.01); *A61B 5/0022* (2013.01); *A61B 5/02055* (2013.01); *G16H 40/67* (2018.01); *A61B 5/021* (2013.01); *A61B 5/024* (2013.01); *A61B 5/0816* (2013.01); *A61B 5/1112* (2013.01); *A61B 5/14542* (2013.01); *A61B 5/318* (2021.01); *A61B 5/4266* (2013.01); *A61B 5/4839* (2013.01); *A61B 5/6801* (2013.01); *A61B 2503/40* (2013.01); *A61B 2560/0219* (2013.01); *A61B 2560/0276* (2013.01); *A61B 2562/08* (2013.01)

(58) Field of Classification Search
CPC .......................... A61B 5/02055; A61B 5/0022
USPC ........................................................ 600/301
See application file for complete search history.

(56) References Cited

U.S. PATENT DOCUMENTS 3,703,890 A 11/1972 Saunders
3,814,095 A 6/1974 Lubens
(Continued)

FOREIGN PATENT DOCUMENTS

CN 109171686 A 1/2019
WO 2007072412 A2 6/2007
(Continued)

OTHER PUBLICATIONS

PCT/US2016/051312, International Search Report and Written Opinion, dated Dec. 27, 2016.
(Continued)

*Primary Examiner* — Niketa I Patel
*Assistant Examiner* — Nathan A Baldwin
(74) *Attorney, Agent, or Firm* — Lee & Hayes, P.C.

(57) ABSTRACT

Aspects of the subject disclosure may include, for example, a system adapted for determining from sensor data collected for a patient over a period of time a normative condition of a biological function of the patient, generating provisioning information according to the normative condition, detecting a first sensor coupled to the patient, and providing the provisioning information to the first sensor to enable the first sensor to detect an abnormal state of the biological function of the patient. Other embodiments are disclosed.

19 Claims, 11 Drawing Sheets

(51) Int. Cl.
    *A61B 5/021*     (2006.01)
    *A61B 5/145*     (2006.01)
    *A61B 5/11*      (2006.01)
    *A61B 5/318*     (2021.01)

(56) References Cited

U.S. PATENT DOCUMENTS

| | | | |
|---|---|---|---|
| 4,290,114 A | 9/1981 | Sinay | |
| 4,329,999 A | 5/1982 | Phillips | |
| D379,356 S | 5/1997 | Liu et al. | |
| 5,688,232 A | 11/1997 | Flower | |
| 5,778,879 A | 7/1998 | Ota et al. | |
| 5,879,292 A | 3/1999 | Sternberg et al. | |
| 5,887,590 A | 3/1999 | Price et al. | |
| 6,238,354 B1 | 5/2001 | Alvarez | |
| 6,526,300 B1 | 2/2003 | Kiani et al. | |
| 7,256,695 B2 | 8/2007 | Hamel et al. | |
| 7,261,691 B1 | 8/2007 | Asomani | |
| 8,315,687 B2 | 11/2012 | Cross et al. | |
| 8,504,323 B2 | 8/2013 | Coradi | |
| 8,529,457 B2 | 9/2013 | Devot et al. | |
| 8,585,607 B2 | 11/2013 | Klap et al. | |
| 8,688,189 B2 | 4/2014 | Shennib | |
| 8,795,174 B2 | 8/2014 | Manicka et al. | |
| 9,566,007 B2 | 2/2017 | McCombie et al. | |
| 10,278,653 B2 | 5/2019 | Otverina et al. | |
| 2001/0034711 A1 | 10/2001 | Tashenberg et al. | |
| 2002/0095092 A1 | 7/2002 | Kondo et al. | |
| 2002/0151934 A1 | 10/2002 | Levine | |
| 2003/0221687 A1 | 12/2003 | Kaigler | |
| 2004/0113771 A1 | 6/2004 | Ozaki et al. | |
| 2004/0153018 A1 | 8/2004 | Brown | |
| 2004/0243006 A1 | 12/2004 | Nakata et al. | |
| 2005/0060198 A1 | 3/2005 | Bayne | |
| 2005/0119711 A1* | 6/2005 | Cho | A61B 5/0205 607/42 |
| 2005/0149362 A1 | 7/2005 | Peterson et al. | |
| 2005/0154264 A1 | 7/2005 | Lecompte et al. | |
| 2005/0215868 A1 | 9/2005 | Kenjou et al. | |
| 2005/0242946 A1 | 11/2005 | Hubbard et al. | |
| 2005/0245852 A1 | 11/2005 | Ellefson et al. | |
| 2006/0002988 A1 | 1/2006 | Ellefson et al. | |
| 2006/0031094 A1 | 2/2006 | Cohen et al. | |
| 2006/0049936 A1 | 3/2006 | Collins et al. | |
| 2006/0066449 A1 | 3/2006 | Johnson | |
| 2006/0122863 A1 | 6/2006 | Gottesman et al. | |
| 2007/0032733 A1 | 2/2007 | Burton | |
| 2007/0049461 A1 | 3/2007 | Kim et al. | |
| 2007/0066526 A1 | 3/2007 | Mochly-Rosen et al. | |
| 2007/0073132 A1 | 3/2007 | Vosch | |
| 2007/0077287 A1 | 4/2007 | Goodrich | |
| 2007/0100219 A1 | 5/2007 | Sweitzer et al. | |
| 2007/0260132 A1 | 11/2007 | Sterling | |
| 2008/0091085 A1 | 4/2008 | Urushihata et al. | |
| 2008/0157980 A1 | 7/2008 | Sachanandani et al. | |
| 2008/0162352 A1 | 7/2008 | Gizewski et al. | |
| 2008/0275311 A1 | 11/2008 | Haq | |
| 2008/0281633 A1 | 11/2008 | Burdea et al. | |
| 2009/0030289 A1 | 1/2009 | Katayama et al. | |
| 2009/0054735 A1 | 2/2009 | Higgins et al. | |
| 2009/0062670 A1 | 3/2009 | Sterling et al. | |
| 2009/0076340 A1 | 3/2009 | Libbus et al. | |
| 2009/0076345 A1 | 3/2009 | Manicka et al. | |
| 2009/0076397 A1 | 3/2009 | Libbus et al. | |
| 2009/0076410 A1 | 3/2009 | Libbus et al. | |
| 2009/0076559 A1 | 3/2009 | Libbus et al. | |
| 2009/0151198 A1 | 6/2009 | Villegas | |
| 2009/0192402 A1 | 7/2009 | Corn et al. | |
| 2009/0209896 A1 | 8/2009 | Selevan | |
| 2009/0227852 A1 | 9/2009 | Glaser | |
| 2009/0292194 A1 | 11/2009 | Libbus et al. | |
| 2009/0326510 A1 | 12/2009 | Haefner et al. | |
| 2010/0049172 A1 | 2/2010 | Chance | |
| 2011/0092780 A1 | 4/2011 | Zhang et al. | |
| 2011/0093210 A1 | 4/2011 | Matsuzaki et al. | |
| 2011/0112416 A1* | 5/2011 | Myr | A61B 5/022 600/509 |
| 2011/0112418 A1* | 5/2011 | Feild | A61B 5/0006 600/509 |
| 2011/0152637 A1 | 6/2011 | Kateraas et al. | |
| 2011/0213217 A1 | 9/2011 | McKenna et al. | |
| 2011/0213625 A1 | 9/2011 | Joao | |
| 2011/0218418 A1 | 9/2011 | Green et al. | |
| 2011/0224498 A1* | 9/2011 | Banet | A61B 5/6824 600/300 |
| 2011/0224506 A1* | 9/2011 | Moon | A61B 5/0002 600/301 |
| 2011/0245695 A1 | 10/2011 | Kawano et al. | |
| 2011/0245711 A1 | 10/2011 | Katra et al. | |
| 2011/0257537 A1 | 10/2011 | Alatriste | |
| 2012/0003933 A1* | 1/2012 | Baker | H04W 76/38 455/41.2 |
| 2012/0029306 A1 | 2/2012 | Paquet et al. | |
| 2012/0029307 A1 | 2/2012 | Paquet et al. | |
| 2012/0029309 A1 | 2/2012 | Paquet et al. | |
| 2012/0029312 A1 | 2/2012 | Beaudry et al. | |
| 2012/0029313 A1 | 2/2012 | Burdett et al. | |
| 2012/0029316 A1 | 2/2012 | Raptis et al. | |
| 2012/0029372 A1 | 2/2012 | Haefner et al. | |
| 2012/0078069 A1 | 3/2012 | Melker | |
| 2012/0130196 A1 | 5/2012 | Jain et al. | |
| 2012/0130203 A1 | 5/2012 | Stergiou et al. | |
| 2012/0179011 A1 | 7/2012 | Moon et al. | |
| 2012/0203078 A1* | 8/2012 | Sze | G06F 19/3418 600/301 |
| 2012/0209084 A1 | 8/2012 | Olsen et al. | |
| 2013/0011819 A1 | 1/2013 | Horseman et al. | |
| 2013/0030259 A1 | 1/2013 | Thomsen et al. | |
| 2013/0072765 A1 | 3/2013 | Kahn et al. | |
| 2013/0073304 A1* | 3/2013 | Kuntagod | G06Q 50/22 705/2 |
| 2013/0085347 A1 | 4/2013 | Manicka et al. | |
| 2013/0123719 A1 | 5/2013 | Mao et al. | |
| 2013/0176115 A1* | 7/2013 | Puleston | H04L 67/04 340/10.51 |
| 2013/0183209 A1 | 7/2013 | Richter et al. | |
| 2013/0192071 A1 | 8/2013 | Esposito et al. | |
| 2013/0204100 A1* | 8/2013 | Acquista | A61B 5/0006 600/301 |
| 2013/0317753 A1* | 11/2013 | Kamen | G06F 19/3412 702/19 |
| 2013/0331665 A1 | 12/2013 | Libbus et al. | |
| 2013/0338448 A1 | 12/2013 | Libbus et al. | |
| 2014/0046144 A1 | 2/2014 | Jayaraman et al. | |
| 2014/0088443 A1 | 3/2014 | Van Den Heuvel et al. | |
| 2014/0107493 A1 | 4/2014 | Yuen et al. | |
| 2014/0176369 A1 | 6/2014 | Choi et al. | |
| 2014/0184422 A1 | 7/2014 | Mensinger et al. | |
| 2014/0266959 A1 | 9/2014 | Xue et al. | |
| 2014/0288396 A1 | 9/2014 | LeBoeuf et al. | |
| 2014/0310298 A1 | 10/2014 | Stivoric et al. | |
| 2014/0330136 A1 | 11/2014 | Manicka et al. | |
| 2015/0073251 A1 | 3/2015 | Mazar | |
| 2015/0094914 A1 | 4/2015 | Abreu | |
| 2015/0126896 A1 | 5/2015 | AlHazme | |
| 2015/0134388 A1 | 5/2015 | Yoo et al. | |
| 2015/0142329 A1 | 5/2015 | Ostman et al. | |
| 2015/0207796 A1* | 7/2015 | Love | G06F 7/58 600/345 |
| 2015/0250426 A1 | 9/2015 | Muehlsteff | |
| 2015/0265212 A1 | 9/2015 | Bruekers et al. | |
| 2015/0302539 A1 | 10/2015 | Mazar et al. | |
| 2015/0335254 A1 | 11/2015 | Fastert et al. | |
| 2016/0051191 A1* | 2/2016 | Miller | G16H 50/30 600/300 |
| 2016/0174903 A1 | 6/2016 | Cutaia | |
| 2016/0198977 A1 | 7/2016 | Eom et al. | |
| 2017/0014085 A1 | 1/2017 | Quinn et al. | |
| 2017/0020461 A1 | 1/2017 | Quinn et al. | |
| 2017/0035306 A1 | 2/2017 | Quinn et al. | |
| 2017/0042467 A1 | 2/2017 | Herr et al. | |
| 2017/0043087 A1 | 2/2017 | Lane | |
| 2017/0065232 A1 | 3/2017 | Lane et al. | |

(56) References Cited

U.S. PATENT DOCUMENTS

| | | | |
|---|---|---|---|
| 2017/0071531 | A1 | 3/2017 | Ehrhart et al. |
| 2017/0112388 | A1 | 4/2017 | Quinn et al. |
| 2017/0112434 | A1 | 4/2017 | Lane |
| 2017/0112451 | A1 | 4/2017 | Meyerson et al. |
| 2017/0112453 | A1 | 4/2017 | Quinn et al. |
| 2017/0172413 | A1 | 6/2017 | Chakravarthy et al. |
| 2017/0346643 | A1* | 11/2017 | Bill .................. H04L 9/3271 |
| 2018/0008207 | A1 | 1/2018 | Sarkela et al. |
| 2018/0035900 | A1 | 2/2018 | Stebbins |
| 2018/0035953 | A1 | 2/2018 | Quinn et al. |
| 2018/0075199 | A1 | 3/2018 | Meyerson et al. |
| 2018/0075204 | A1 | 3/2018 | Lee et al. |
| 2018/0116560 | A1 | 5/2018 | Quinn et al. |
| 2019/0117080 | A1 | 4/2019 | Ma et al. |

FOREIGN PATENT DOCUMENTS

| | | |
|---|---|---|
| WO | 2011094819 A1 | 8/2011 |
| WO | 2012140537 A1 | 10/2012 |
| WO | 2014031944 A1 | 2/2014 |
| WO | 2014063160 A1 | 4/2014 |
| WO | 2014153017 A1 | 9/2014 |
| WO | 2014160764 A1 | 10/2014 |

OTHER PUBLICATIONS

"Texas Instruments launches industry's first highly integrated NFC sensor transponder for industrial, medical, wearables and Internet of Things. (IoT) applications", Texas Instruments News Releases, Apr. 10, 2015, 2 pages.

Borreli, Lizette , "Smartphone Stress Hormone Test App May Be Able to Measure Cortisol Levels: What Are Signs of Stress?", Medical. Daily, Jul. 7, 2014, 2 pages.

Forkan, Abdur et al., "Context-aware Cardiac Monitoring for Early Detection of Heart Diseases", Computing in Cardiology; 40, 2013, 277-280.

Jovanov, Emil et al., "A wireless body area network of intelligent motion sensors for computer assisted physical rehabilitation", Journal of NeuroEngineering and Rehabilitation, 2005, 10 pages.

Jovanov, Emil et al., "Stress Monitoring Using a Distributed Wireless Intelligent Sensor System", IEEE Engineering in Medicine and Biology Magazine, 2003.

Sano, Akane et al., "Stress Recognition Using Wearable Sensors and Mobile Phones", Humaine Association Conference on Affective Computing and Intelligent Interaction, 2013, 6 pages.

Sun, Feng-Tso , "Activity-aware Mental Stress Detection Using Physiological Sensors", Carnegie Mellon University, 2015, 20 pages.

Talbot, David , "Wrist Sensor Tells You How Stressed Out You Are", MIT Technology Review, Dec. 20, 2012, 4 pgs.

Non Final Office Action dated Mar. 22, 2019 for U.S. Appl. No. 14/960,872 "Method and Apparatus for Detecting a Biological condition from a Comparative Measurement" Meyerson, 21 pages.

Office Action for U.S. Appl. No. 15/2578,212, dated Feb. 4, 2019, Quinn et al., "Method and Apparatus for Monitoring a Functional Capacity of an Individual", 16 pages.

Office Action for U.S. Appl. No. 14/920,200, dated Feb. 8, 2019, Quinn et al., "Method and Apparatus for Performing Biological Measurements", 16 pages.

Office Action for U.S. Appl. No. 15/207,689, dated Oct. 11, 2019, Quinn, "Method and Apparatus for Detecting a Biological Condition", 16 pages.

Office Action for U.S. Appl. No. 14/960,872, dated Sep. 20, 2019, Meyerson, "Method and Apparatus for Detecting a Biological Condition from a Comparative Measurement", 20 pages.

Office Action for U.S. Appl. No. 14/920,200, dated Dec. 20, 2019, Quinn, "Method and Apparatus for Performing Biological Measurements", 18 pages.

Office Action for U.S. Appl. No. 15/207,689, dated Feb. 13, 2020, Quinn, "Method and Apparatus for Detecting a Biological Condition", 19 pages.

Office Action for U.S. Appl. No. 14/960,872, dated Feb. 24, 2020, Meyerson, "Method and Apparatus for Detecting a Biological Condition from a Comparative Measurement", 19 pages.

Office Action for U.S. Appl. No. 15/207,689, dated May 21, 2020, Quinn, "Method and Apparatus for Detecting a Biological Condition," 19 pages.

Office Action for U.S. Appl. No. 14/960,872, dated Jun. 29, 2020, Meyerson, "Method and Apparatus for Detecting a Biological Condition from a Comparative Measurement", 20 pages.

Patent Cooperation Treaty, "International Preliminary Report on Patentability dated May 3, 2018", for PCT Application No. PCT/US16/51312, dated May 3, 2018, 9 pages.

Perumal, Veeradasan et al., "Advances in Biosensors: Principle, Architecture and Applications", Institute of Nano Electronic Engineering (INEE), University of Malaysai Perlis (UniMAP), Perlis, Malaysia, Elsevier, Dec. 2, 2013, 15 pages.

* cited by examiner

102

500

METHOD AND APPARATUS FOR MANAGING SENSORS

FIELD OF THE DISCLOSURE

The subject disclosure relates to managing sensor data collected by a system.

BACKGROUND

Biological sensors can be used for measuring temperature, respiration, pulse rate, blood pressure, among other things. Some biological sensors can be implanted and can be configured to be battery-less. Battery-less sensors can utilize one or more antennas to receive radio frequency signals, and which can be converted to energy that powers components of the sensor while the radio frequency signals are present. Some biological sensors can also be configured to deliver dosages of a controlled substance.

BRIEF DESCRIPTION OF THE DRAWINGS

Reference will now be made to the accompanying drawings, which are not necessarily drawn to scale, and wherein.

DETAILED DESCRIPTION

The subject disclosure describes, among other things, illustrative embodiments for managing sensor data and usage of sensors generating the sensor data. Other embodiments are described in the subject disclosure.

One or more aspects of the subject disclosure include a system having a processor, and a memory that stores executable instructions that, when executed by the processor, facilitate performance of operations, including obtaining first provisioning information associated with a first sensor coupled to a first patient, the first sensor used for measuring a biological data of the first patient, detecting a second sensor coupled to the first patient, determining that the first sensor is being replaced by the second sensor, determining that the second sensor does not have the first provisioning information associated with the first sensor, and providing a copy of the first provisioning information of the first sensor to the second sensor.

One or more aspects of the subject disclosure include a machine-readable storage medium, storing executable instructions that, when executed by a processor, facilitate performance of operations, including determining from sensor data collected for a patient over a period of time a normative condition of a biological function of the patient, generating provisioning information according to the normative condition, detecting a first sensor coupled to the patient, and providing the provisioning information to the first sensor to enable the first sensor to detect an abnormal state of the biological function of the patient.

One or more aspects of the subject disclosure include a method for determining from sensor data collected for a patient over a period of time a normative condition of a biological function of the patient, generating provisioning information according to the normative condition, detecting a first sensor coupled to the patient, and providing the provisioning information to the first sensor to enable the first sensor to detect an abnormal state of the biological function of the patient.

Figure 1:
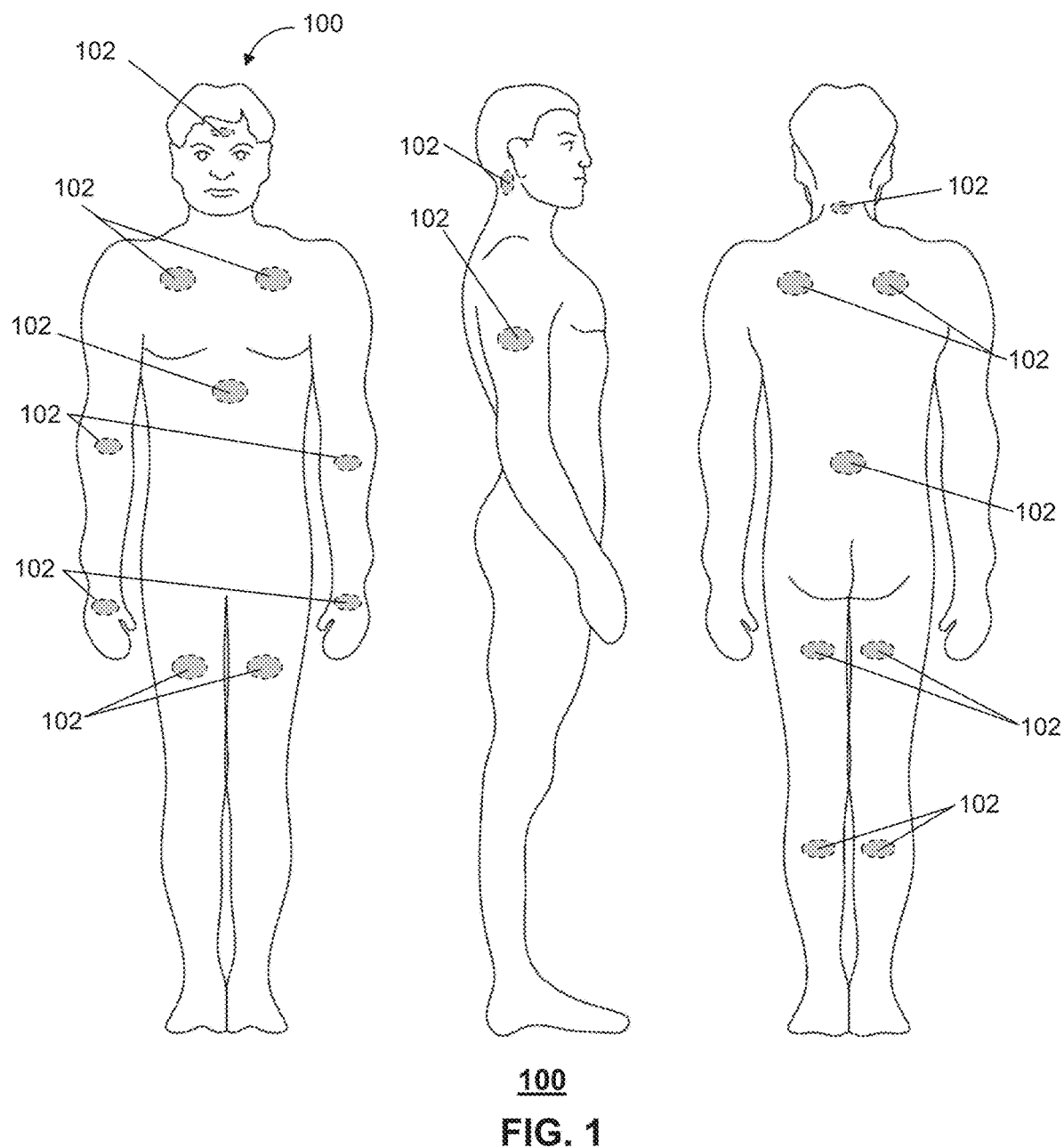
FIG. 1 is a block diagram illustrating example, non-limiting embodiments for placing sensors on a patient in accordance with various aspects of the subject disclosure described herein.

Turning now to FIG. 1, a block diagram illustrating example, non-limiting embodiments for placing biological sensors 102 on a patient 100 in accordance with various aspects of the subject disclosure is shown. FIG. 1 depicts a number of non-limiting illustrations of locations where biological sensors 102 can be placed on a patient 100. For example, biological sensors 102 can be placed on a patient's forehead, chest, abdomen, arms, hands, front or rear section of a thigh, behind an ear, on a side of an arm, neck, back, or calves as illustrated in FIG. 1. Other locations for placement of biological sensors 102 are possible and contemplated by the subject disclosure.

Figure 2A:
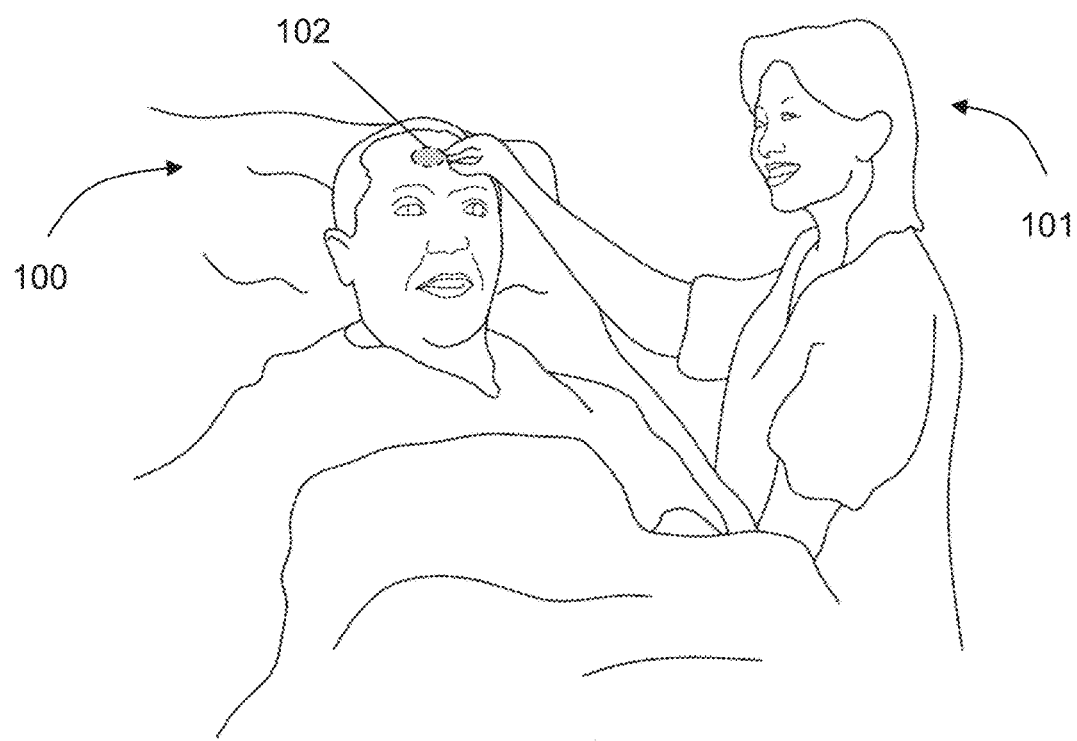
FIGS. 2A-2B are block diagrams illustrating example, non-limiting embodiments for managing use of one or more sensors of a patient in accordance with various aspects of the subject disclosure described herein.
Figure 2B:
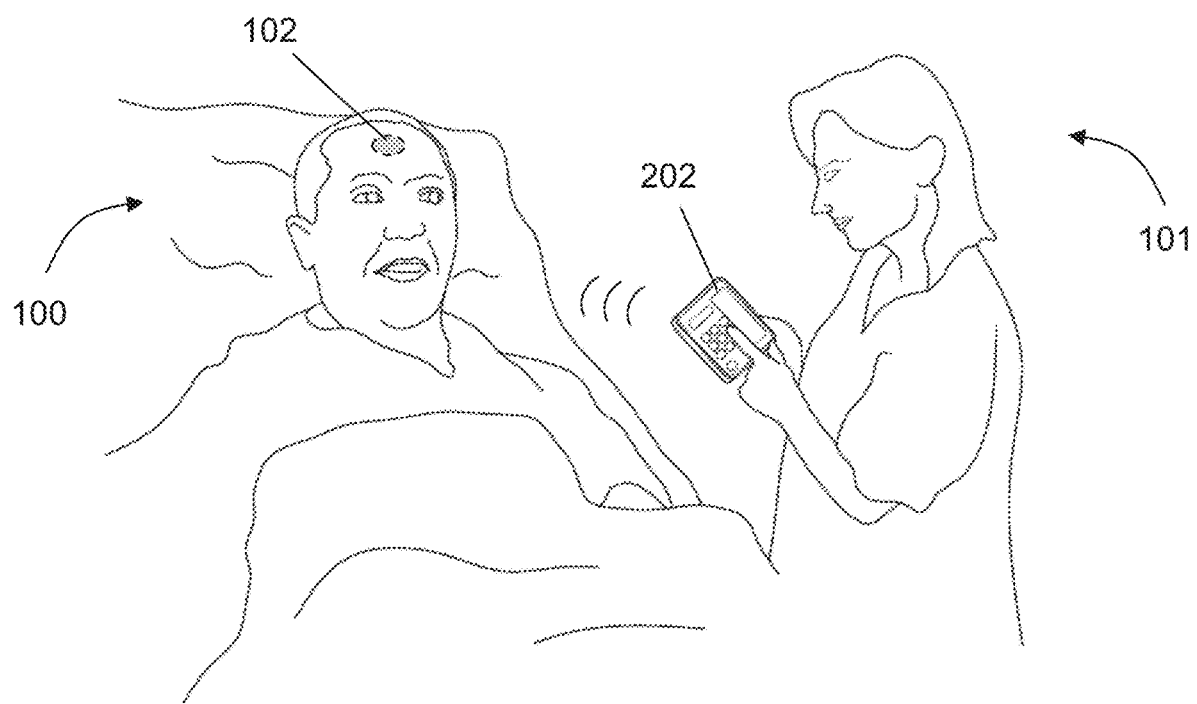

The biological sensors 102 can be placed or managed by a nurse 101 as shown in FIGS. 2A-2B. A nurse 101 can, for example, place a biological sensor 102 on the patient 100 as depicted in FIG. 2A and manage use of the biological sensor 102 with a computing device 202 such as a touch-screen tablet as depicted in FIG. 2B. The computing device 202 can also be represented by a smartphone, a laptop computer, or other suitable computing devices. The computing device 202 can be communicatively coupled to the biological sensor 102 by a wireless interface, such as, near field communications (NFC) having, for example, a range of 3-4 inches from the biological sensor 102, Bluetooth®, ZigBee®, WiFi, or other suitable short range wireless technology. Alternatively, the computing device 202 can be communicatively coupled to the biological sensor 102 by a wired interface or tethered interface (e.g., a USB cable).

Biological sensors 102 can be placed on an outer surface of a skin of the patient 100 with an adhesive, or can be implanted in the patient 100. Although the patient 100 is shown to be a human patient, a patient 100 can also be represented by a non-human species (e.g., a dog, a cat, a horse, cattle, a tiger, etc.) or any other type of biological organism which can use a biological sensor 102. Biological sensors 102 can be used for a number of functions such as, for example, electrocardiogram measurements, measuring temperature, perspiration, pulse rate, blood pressure, respiration rate, glucose levels in blood, peripheral capillary oxygen saturation (SpO2), and other measurable biological functions contemplated by the subject disclosure.

The biological sensors 102 can also be adapted to store measurements, compare measurements to biological markers to detect a biological condition, and to report such measurements and detected conditions. Biological sensors 102 are, however, not limited to monitoring applications. For example, biological sensors 102 can also be adapted to deliver controlled dosages of medication using, for example, micro-needles. Such sensors can also perform measurements to monitor a biological response by the patient 100 to the medication delivered, record and report measurements, frequency of dosages, amount of dosage delivered, and so on. The reports can also include temporal data such as day, month, year, time when measurement was performed and/or time when medication was delivered.

Figure 3A:
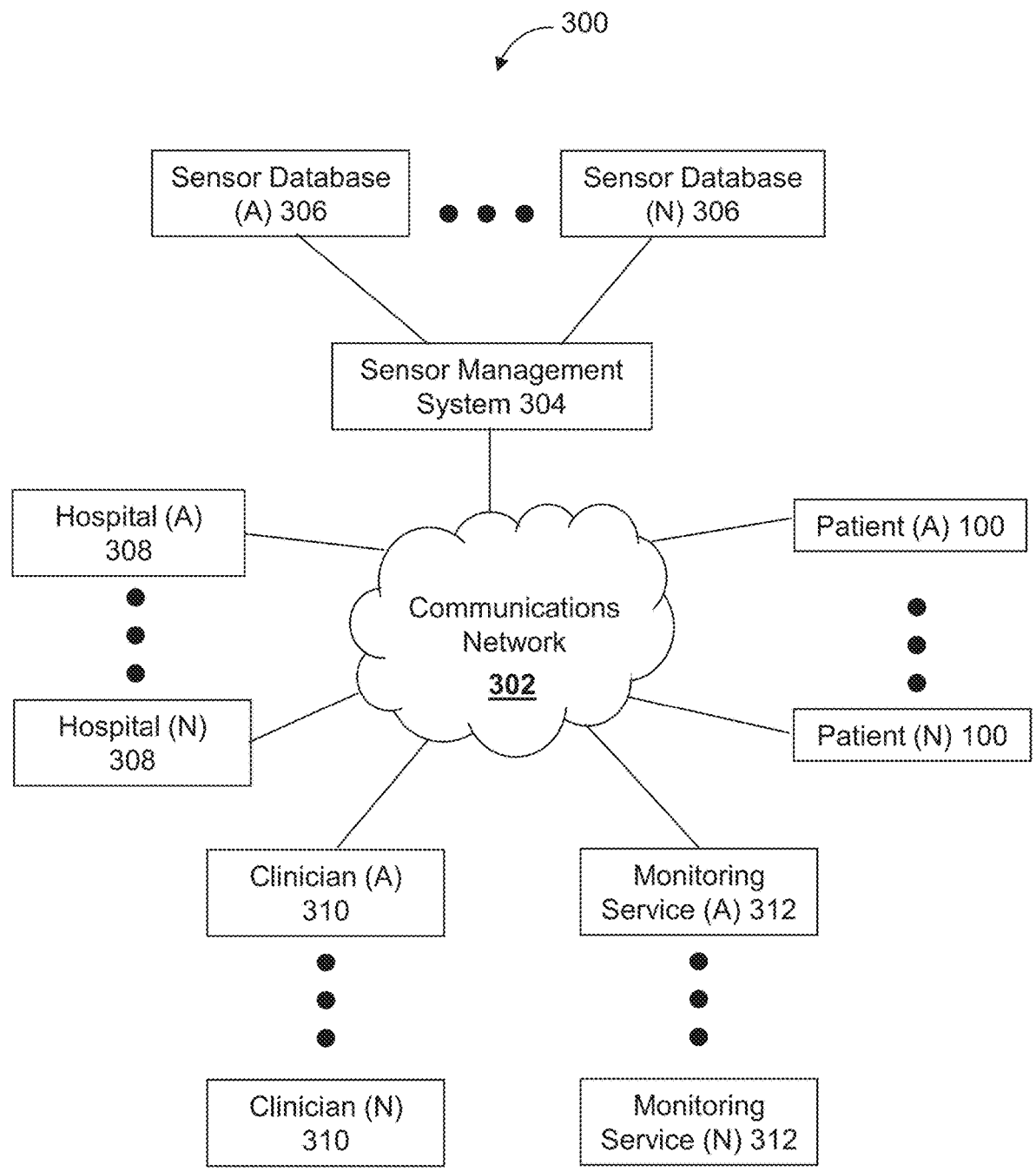
FIGS. 3A-3F are block diagrams illustrating example, non-limiting embodiments of a system for managing sensor data in accordance with various aspects of the subject disclosure described herein.
Figure 3B:
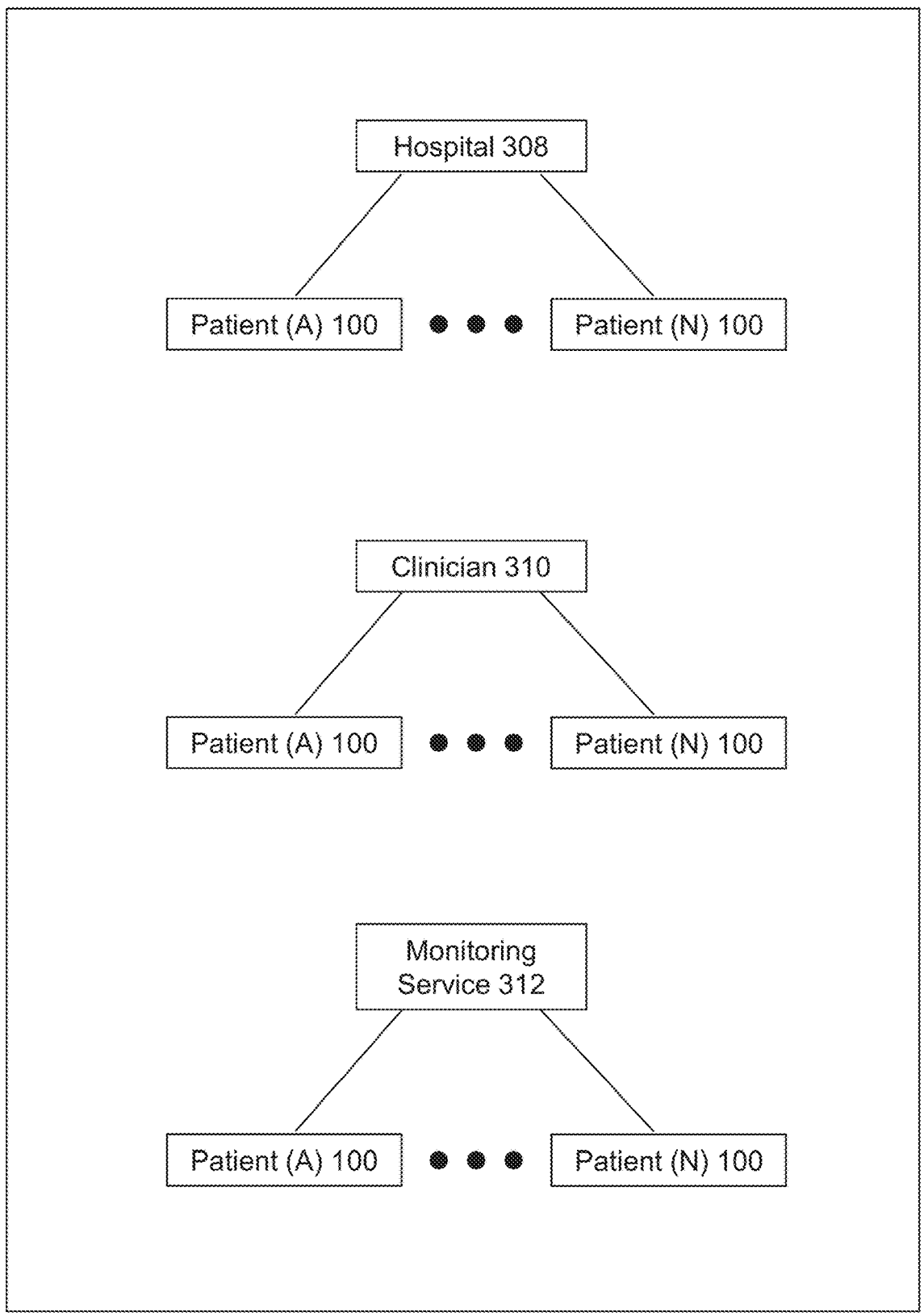

Turning now to FIGS. 3A-3F, block diagrams illustrating example, non-limiting embodiments of a system 300 for managing sensor data in accordance with various aspects of the subject disclosure is shown. FIG. 3A depicts a network architecture in which one or more sensor management systems 304 are communicatively coupled to hospitals (A)-(N) 308, clinicians (A)-(N) 310, monitoring services (A)-(N) 312, and/or patients (A)-(N) 100, singly or in combination. The sensor management system 304 can record and access data from sensor databases (A)-(N) 306. In an embodiment, hospitals (A)-(N) 308, clinicians (A)-(N) 310, and monitoring services (A)-(N) 312 can provide the sensor management system 304 access to patients 100 through their systems and local network devices as depicted in FIG. 3B. Alternatively, the sensor management system 304 can be communicatively coupled to patients (A)-(N) 100 directly as shown in FIG. 3A without intervening health care providers (such as hospitals, clinicians, or monitoring services), and instead provide care providers access to information of certain patients recorded in the sensor databases (A)-(N) 306.

Figure 3C:
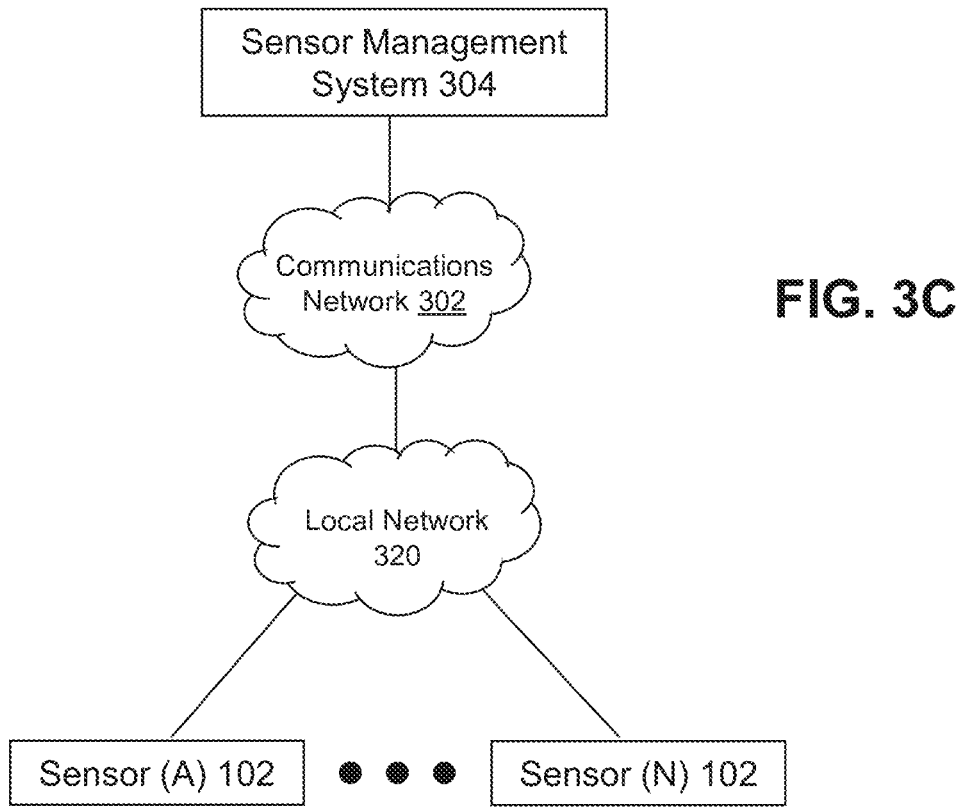
Figure 3D:
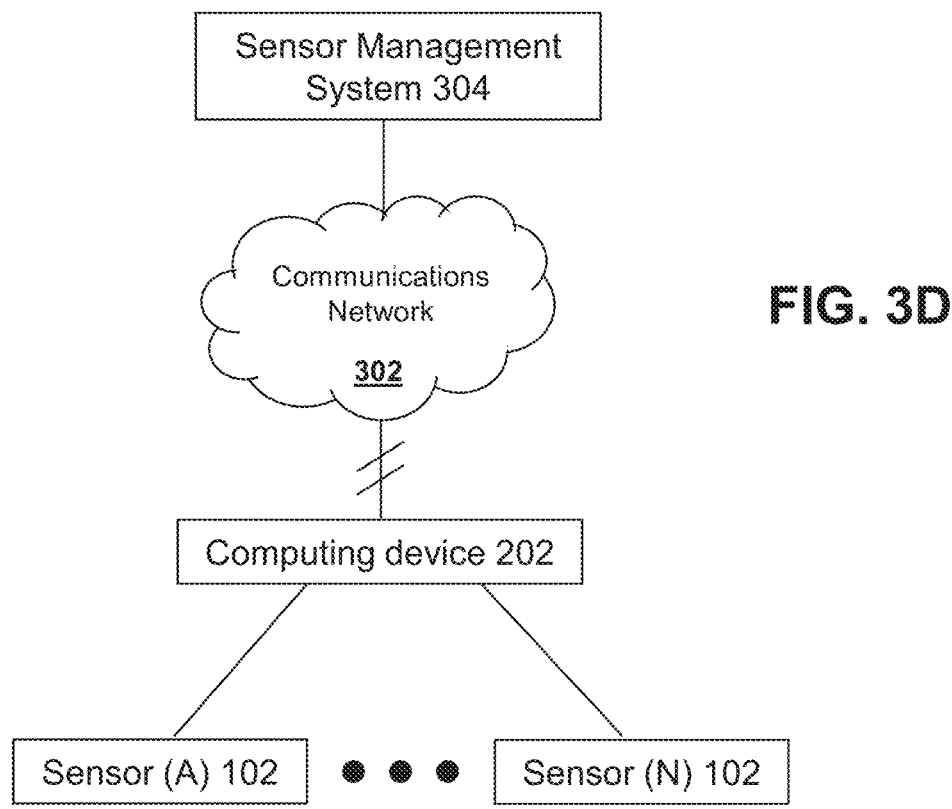

FIGS. 3C-3F depict different arrangements for managing sensors 102. In one embodiment, for example, the sensor management system 304 can be communicatively coupled to sensors 102 via the communications network 302 which is communicatively coupled to a local network 320 (e.g., a local area network, WiFi access point, etc.) having access to the sensors 102 as depicted in FIG. 3C. In another embodiment, the sensor management system 304 can be communicatively coupled to sensors 102 via the communications network 302 which is communicatively coupled to a computing device 202 (such as shown in FIG. 2B) having access to the sensors 102 as depicted in FIG. 3D. In some embodiments, the computing device 202 can operate off-line (i.e., without access to the sensor management system 304) as depicted in FIG. 3D with the hash lines. While off-line, the computing device 202 can collect sensor data from sensors 102, provision sensors 102, and perform other tasks which can be recorded locally in a memory of the computing device 202. Once the computing device 202 restores access to the sensor management system 304 via communications network 302, the computing device 202 can provide the sensor management system 302 access to its local memory to update databases 306 with new sensor data, provisioning data, and so on.

Figure 3E:
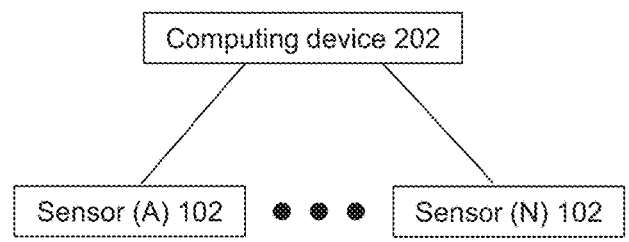
Figure 3F:
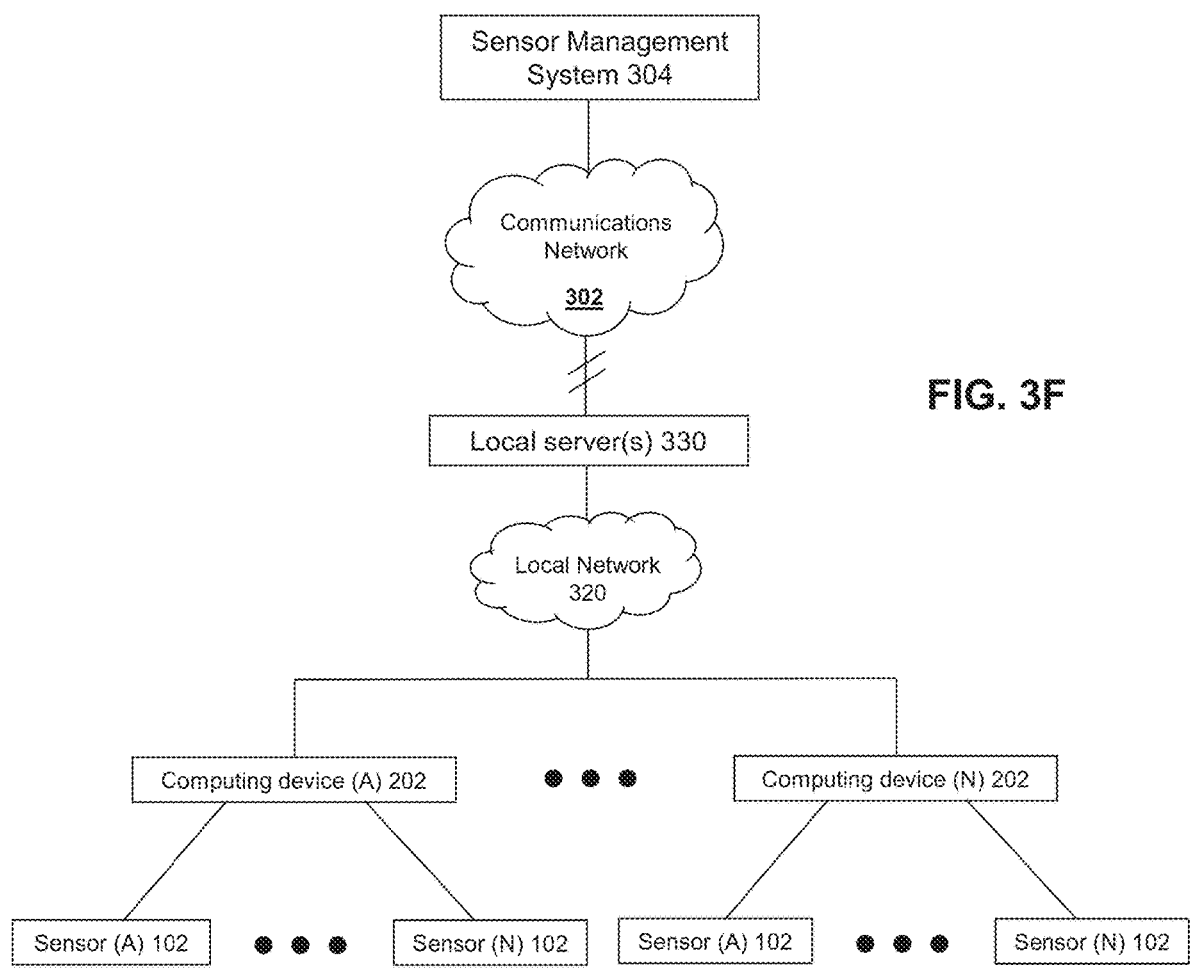

In yet another embodiment, the computing device 202 can be configured to operate independently from the sensor management system 304 as depicted in FIG. 3E and collect sensor data from sensors 102, provision sensors 102, and perform other tasks which are recorded locally in the memory of the computing device 202. In another embodiment, the sensor management system 304 can be configured to communicate with one or more local servers 330 as depicted in FIG. 3F which have access to computing devices 202 via a local network 320. The computing devices 202 can provide sensor management information to the local servers 330. The local servers 330 in turn can provide the sensor management system 304 access to the sensor information collected from the computing devices 202. In some embodiments, the local servers 330 can also be configured to operate independently from the sensor management system 304.

It will be appreciated from the number of illustrations shown in FIGS. 3A-3F that any number of network configurations between sensors 102 and other devices managing use of the sensors 102 is possible. It is further noted that the arrangements in FIGS. 3A-3F can be adapted for managing sensors worn by a patient located in a residence, a clinic, a doctor's office, a hospital, outdoors, while in transit, while traveling, and so on.

It is also noted that the communications network 302 and the local network 320 shown in FIGS. 3A-3F can comprise a landline communications network (e.g., packet switched landline networks, circuit switched networks, etc.), a wireless communications network (e.g., cellular communications, WiFi, etc.), or combinations thereof. It is also noted that the computing device 202 of FIG. 2B can be configured to initiate communications with the biological sensor 102 and the communications network 302 to provide the sensor management system 304 access to the biological sensors 102 used by multiple patients. In this embodiment, the computing device 202 can serve as a gateway between the communications network 302 and the biological sensors 102. In other embodiments, the biological sensors 102 can gain direct access to the communications network 302 by way of a gateway that provide internet access (e.g., a WiFi access point).

The sensor management system 304 can be configured to store endless amounts of biological data of patients 100 over long periods of time (e.g., an entire lifetime and/or generations of patients) in databases 306. Such data can serve to provide historical information that may be invaluable to the patients 100 and their lineages.

Figure 4:
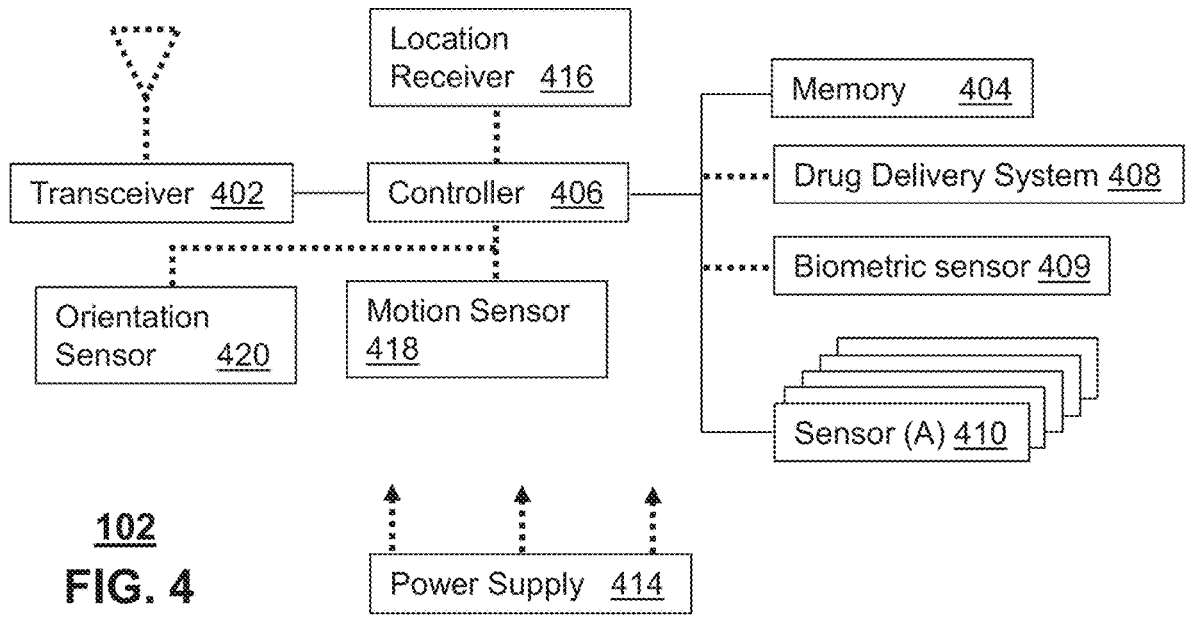
FIG. 4 is a block diagram illustrating an example, non-limiting embodiment of a biological sensor in accordance with various aspects of the subject disclosure described herein.

Turning now to FIG. 4, a block diagram illustrating an example, non-limiting embodiment of a biological sensor 102 is shown. The biological sensor 102 can comprise a wireline and/or wireless transceiver 402 (herein transceiver 402), a power supply 414, a location receiver 416, a motion sensor 418, an orientation sensor 420, a memory 404, a drug delivery system 408, a biometric sensor 409, one or more sensors 410, and a controller 406 for managing operations thereof. Not all of the components shown in the biological sensor 102 are necessary. For example, in one embodiment the biological sensor 102 can comprise the transceiver 402, the controller 406, the memory 404, one or more sensors 410, and the power supply 404. In other embodiments, the biological sensor 102 can further include one or more components not used in the previous embodiment such as the drug delivery system 408, the biometric sensor 409, the location receiver 416, the motion sensor 418, the orientation senor 420, or any combinations thereof. Accordingly, any combinations of component of the biological sensor 102 depicted in FIG. 4 are possible and contemplated by the subject disclosure.

Although FIGS. 1 and 2A-2B depict topical applications of the biological sensor 102 on an outer skin of the patient 100, in other embodiments, the biological sensor 102 can in whole or in part be embedded in a patient 100. For example, a certain sensor 410 may be embedded in a skin of the patient 100 while other components of the biological sensor 102 may be located on an outer surface of the skin. In other embodiments, a certain sensor 410 may be attached to an organ (e.g., the heart). Accordingly, the biological sensor 102 can be located in a number of places within a patient's body, outside a patient's body, or combinations thereof.

The transceiver 402 can support short-range or long-range wireless access technologies such as RFID, Near Field Communications (NFC), Bluetooth®, ZigBee®, WiFi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 402 can also be adapted to support cable protocols (e.g., USB, Firewire, Ethernet, or other suitable cable technologies), circuit-switched wireline access technologies (such as PSTN), packet-switched wireline access technologies (such as TCP/IP, VoIP, etc.), or combinations thereof.

The drug delivery system 408 can comprise micro-needles, one or more reservoirs of one or more drugs, and a piezo inkjet (not shown). The piezo inkjet can be coupled to the one or more reservoirs to selectively deliver dosages via the micro-needles. The piezo inkjet can be coupled to the controller 406 which can provide controlled delivery of dosages of one or more drugs by the drug delivery system 408. The biometric sensor 409 can be a fingerprint sensor, a voice sensor (with a built-in microphone), or any other type of suitable biometric sensor for identifying a user of the biological sensor 102. The sensors 410 can use common biological sensing technology for measuring biological functions of a patient including, but not limited to, temperature, perspiration, pulse rate, blood pressure, respiration rate, glucose levels in the blood, SpO2, ECG/EKG, and so on.

The power supply 414 can utilize common power management technologies such as replaceable and rechargeable batteries, supply regulation technologies, and/or charging system technologies for supplying energy to the components of the biological sensor 102 to facilitate long-range or short-range portable applications. Alternatively, or in combination, the power supply 414 can utilize external power sources such as DC power supplied over a physical interface such as a USB port or other suitable tethering technologies.

In other embodiments, the biological sensor can be battery-less. In this embodiment, the power supply 414 can utilize circuitry that powers the components of the biological sensor 102 utilizing RF energy received by an antenna or other receptive element. In one embodiment, for example, the biological sensor 102 can use NFC technology to intercept RF signals generated by the computing device 202 when the computing device 202 is held a few inches away from the biological sensor 102. In another embodiment, the biological sensor 102 can utilize battery-less technology similar to that used by passive RFID devices. Other suitable battery-less technologies can be applied to the embodiments of the subject disclosure.

The location receiver 416 can utilize location technology such as a global positioning system (GPS) receiver capable of identifying a location of the biological sensor 102 using signals generated by a constellation of GPS satellites. The motion sensor 418 can utilize motion sensing technology such as an accelerometer, a gyroscope, or other suitable motion sensing technology to detect a motion of the biological sensor 102 in three-dimensional space. The orientation sensor 420 can utilize orientation sensing technology such as a magnetometer to detect the orientation of the biological sensor 102 (north, south, west, east, as well as combined orientations in degrees, minutes, or other suitable orientation metrics).

The controller 406 can utilize computing technologies such as a microprocessor, a digital signal processor (DSP), programmable gate arrays, application specific integrated circuits, which can be coupled to the memory 404. The memory 404 can utilize memory technologies such as Flash, ROM, RAM, SRAM, DRAM or other storage technologies for executing instructions, controlling operations of the biological sensor 102, and for storing and processing sensing data supplied by the aforementioned components of the biological sensor 102.

Figure 5:
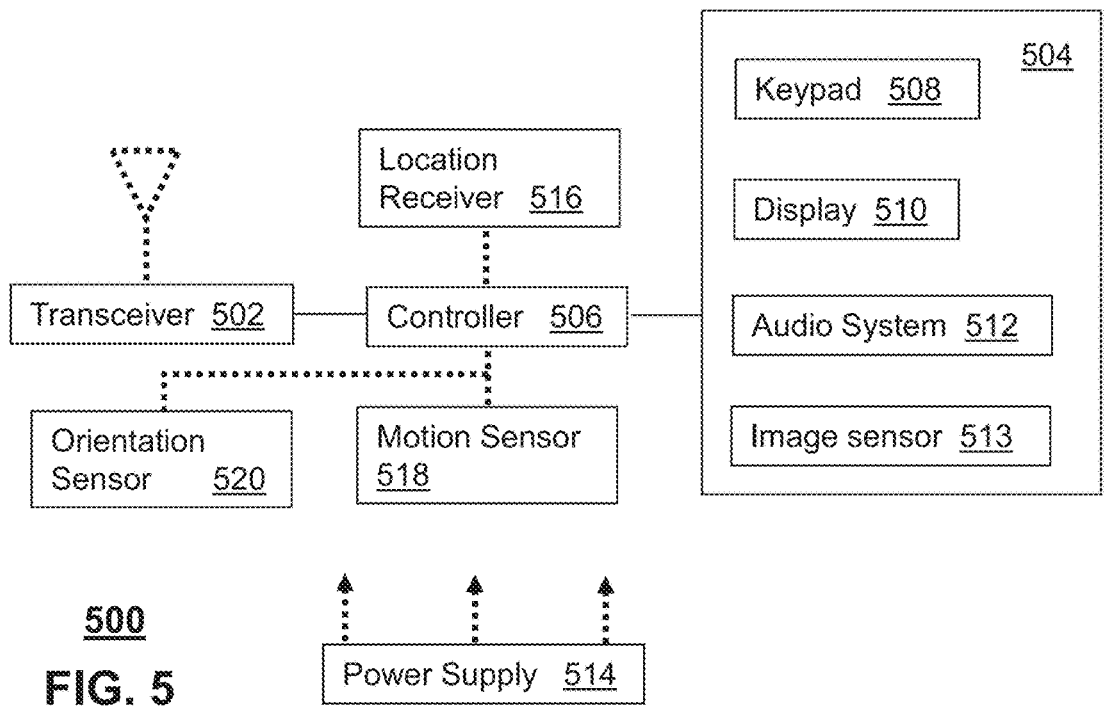
FIG. 5 is a block diagram illustrating an example, non-limiting embodiment of a computing device in accordance with various aspects of the subject disclosure described herein.

Turning now to FIG. 5, a block diagram illustrating an example, non-limiting embodiment of a computing device 202 in accordance with various aspects of the subject disclosure is shown. Computing device 202 can comprise a wireline and/or wireless transceiver 502 (herein transceiver 502), a user interface (UI) 504, a power supply 514, a location receiver 516, a motion sensor 518, an orientation sensor 520, and a controller 506 for managing operations thereof. The transceiver 502 can support short-range or long-range wireless access technologies such as Bluetooth®, ZigBee®, WiFi, DECT, or cellular communication technologies, just to mention a few. Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 502 can also be adapted to support circuit-switched wireline access technologies (such as PSTN), packet-switched wireline access technologies (such as TCP/IP, VoIP, etc.), and combinations thereof.

The UI 504 can include a depressible or touch-sensitive keypad 508 with a navigation mechanism such as a roller ball, a joystick, a mouse, or a navigation disk for manipulating operations of the computing device 202. The keypad 508 can be an integral part of a housing assembly of the computing device 202 or an independent device operably coupled thereto by a tethered wireline interface (such as a USB cable) or a wireless interface supporting for example Bluetooth®. The keypad 508 can represent a numeric keypad commonly used by phones, and/or a QWERTY keypad with alphanumeric keys. The UI 504 can further include a display 510 such as monochrome or color LCD (Liquid Crystal Display), OLED (Organic Light Emitting Diode) or other suitable display technology for conveying images to an end user of the computing device 202. In an embodiment where the display 510 is touch-sensitive, a portion or all of the keypad 508 can be presented by way of the display 510 with navigation features.

In another embodiment, display 510 can use touch screen technology to serve as a user interface for detecting user input. As a touch screen display, the computing device 202 can be adapted to present a user interface with graphical user interface (GUI) elements that can be selected by a user with a touch of a finger. The touch screen display 510 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 510 can be an integral part of the housing assembly of the computing device 202 or an independent device communicatively coupled thereto by a tethered wireline interface (such as a cable) or a wireless interface.

The UI 504 can also include an audio system 512 that utilizes audio technology for conveying low volume audio (such as audio heard in proximity of a human ear) and high volume audio (such as speakerphone for hands free operation). The audio system 512 can further include a microphone for receiving audible signals of an end user. The audio system 512 can also be used for voice recognition applications. The UI 504 can further include an image sensor 513 such as a charged coupled device (CCD) camera for capturing still or moving images.

The power supply 514 can utilize common power management technologies such as replaceable and rechargeable batteries, supply regulation technologies, and/or charging system technologies for supplying energy to the components of the computing device 202 to facilitate long-range or short-range portable applications. Alternatively, or in combination, the charging system can utilize external power sources such as DC power supplied over a physical interface such as a USB port or other suitable tethering technologies.

The location receiver 516 can utilize location technology such as a GPS receiver for identifying a location of the computing device 202 based on signals generated by a constellation of GPS satellites, which can be used for facilitating location services such as navigation. The motion sensor 518 can utilize motion sensing technology such as an accelerometer, a gyroscope, or other suitable motion sensing technology to detect motion of the computing device 202 in three-dimensional space. The orientation sensor 520 can utilize orientation sensing technology such as a magnetometer to detect the orientation of the computing device 202 (north, south, west, and east, as well as combined orientations in degrees, minutes, or other suitable orientation metrics).

The controller 506 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the computing device 202.

Other components not shown in FIG. 5 can be used in one or more embodiments of the subject disclosure. For instance, the computing device 202 can also include a slot for adding or removing an identity module such as a Subscriber Identity Module (SIM) card. SIM cards can be used for identifying subscriber services, executing programs, storing subscriber data, and so forth. The computing device 202 as described herein can operate with more or less of the circuit components shown in FIG. 5. These variant embodiments can be used in one or more embodiments of the subject disclosure.

Figure 6:
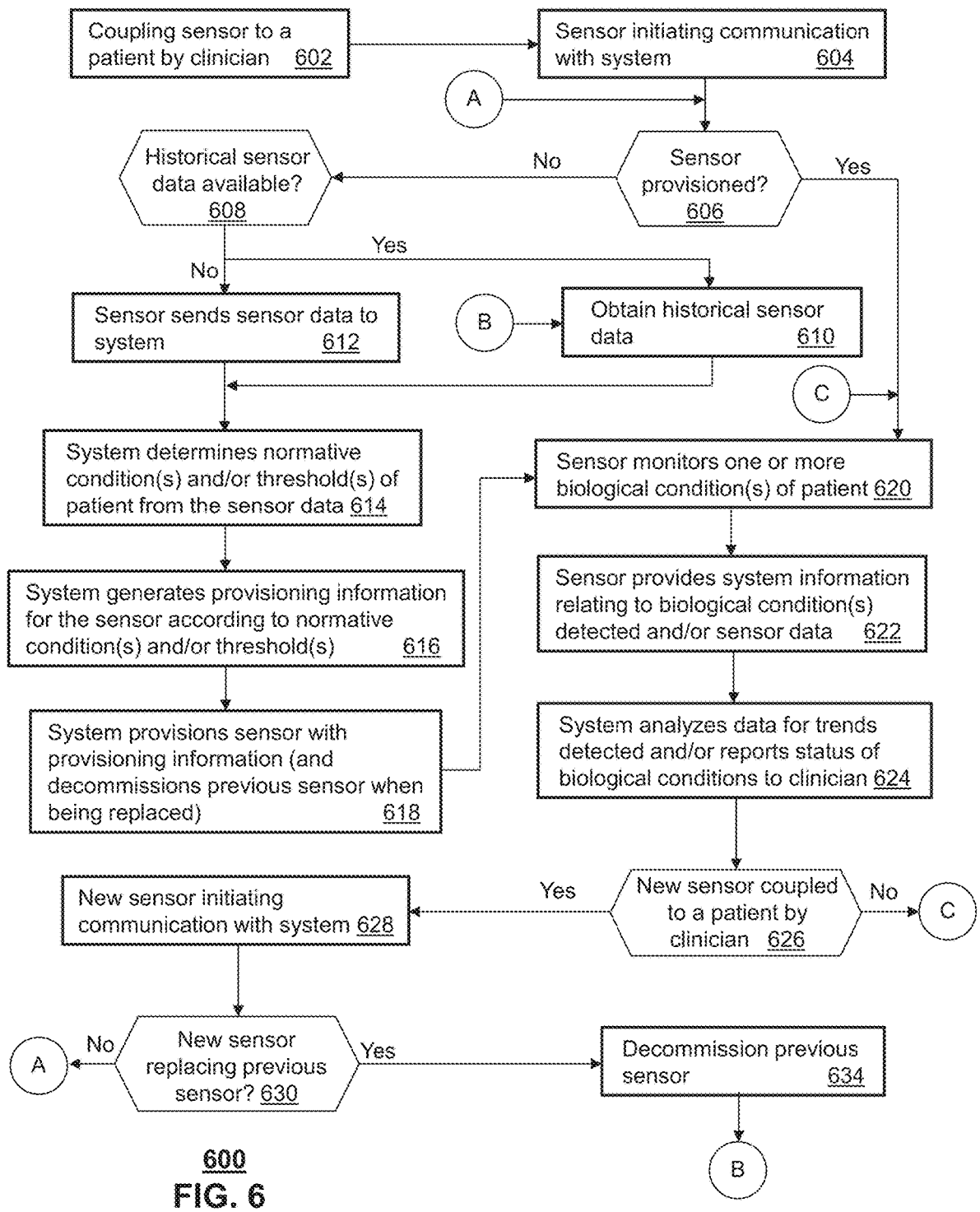
FIG. 6 is a block diagram illustrating an example, non-limiting embodiment of a method in accordance with various aspects of the subject disclosure described herein.

Turning now to FIG. 6, a block diagram illustrating an example, non-limiting embodiment of a method 600 in accordance with various aspects of the subject disclosure is shown. Method 600 can be applied to any combination of the embodiments of FIGS. 1, 2A-2B, 3A-3B, and 4-5. Method 600 can begin with step 602 where a clinician (e.g., a nurse as shown in FIG. 2A), places a biological sensor 102 on a patient 100. In one embodiment, the biological sensor 102 can utilize an adhesive for coupling to the skin of the patient 100. In another embodiment, the clinician can be a surgeon that implants the biological sensor 102 in whole or in part in a body portion of the patient 100.

At step 604, the biological sensor 102 can be configured to initiate communications with a system. In one embodiment the biological sensor 102 can initiate communications with a computing device 202 such as shown in FIG. 2B. In this embodiment, the biological sensor 102 can initiate communications utilizing, for example, short range wireless technology such as near field communications (NFC), Bluetooth®, ZigBee®, WiFi or other suitable short range wireless communications technology. The computing device 202 in turn can communicate with the sensor management system 304 via the communications network 302 to provide the sensor management system 304 access to information supplied by the biological sensor 102.

In another embodiment, the biological sensor 102 can initiate communications with the sensor management system 304 by way of the communications network 302 utilizing long range wireless technology such cellular technology or other suitable long range wireless communications technology. In yet another embodiment, the biological sensor 102 can initiate communications with the sensor management system 304 by way of the communications network 302 utilizing wireline communications technology.

In one embodiment, for example, the biological sensor 102 can be tethered to the computing device 202 with a cable (e.g., a USB cable). In this embodiment, the computing device 202 can provide the sensor management system 304 access to information supplied by the biological sensor 102. In another embodiment, the biological sensor 102 can have access to a local network providing connectivity to the Internet by way of a cable (e.g., Ethernet cable). In this embodiment, the sensor management system 304 can have direct access to the biological sensor 102.

Based on the foregoing embodiments, the system referred to in step 604 and in subsequent steps can be represented by the computing device 202, the sensor management system 304, or a combination thereof. The term system as utilized in method 600 can be adapted to represent solely the computing device 202, solely the sensor management system 304, or a combination of the computing device 202 and the sensor management system 304, each configured to cooperate therebetween in a manner that achieves the embodiments described by method 600. It is also noted that other arrangements are possible as shown in FIGS. 3A-3F.

At step 606, the system can determine whether the biological sensor 102 is provisioned. This determination can be made a number of ways. For example, a clinician 101 can enter information on a computing device 202 which signals the sensor management system 304 that the biological sensor 102 is a new sensor placed on patient 100, which has not been provisioned. In another embodiment, the biological sensor 102 can be polled by the sensor management system 304 (or by the computing device 202) to determine if the biological sensor 102 has been provisioned. In another embodiment, the sensor management system 304 (and/or the computing device 202) can be configured to determine that a prior biological sensor 102 has been used (or is currently in use) by the patient 100 and the new biological sensor 102 that was detected is of a different serial number, but functionally equivalent or similar to the prior biological sensor 102.

In another embodiment, the sensor management system 304 (or the computing device 202) can be configured to receive from the biological sensor 102 an identification of the patient 100. To obtain this information, the biological sensor 102 can be configured to receive the identification of the patient 100 from the computing device 202. In another embodiment, the biological sensor 102 can obtain the identification from a wristband worn by the patient 100 that includes an RFID device or other device suitable to convey the identification of the patient 100 wirelessly to the biological sensor 102. Upon obtaining the identification of the patient 100, the sensor management system 304 (or the computing device 202) can be configured to retrieve a record of the patient 100 indexed according to the identification of the patient, and detect therefrom that the biological sensor 102 is not identified in a chart of the patient 100.

In yet another embodiment, the sensor management system 304 (or the computing device 202) can be configured to detect an expiration of a utilization period applied to a prior biological sensor 102 and determine that the biological sensor 102 now detected is a replacement sensor that has not been provisioned. There are many other ways to perform inventory management of biological sensors 102 to determine when the biological sensor 102 is not provisioned. For example, the sensor management system 304 (or the computing device 202) can be configured to detect that provisioning data stored by the sensor management system 304 (or the computing device 202) is not synchronized with data stored in the biological sensor 102 by comparing time stamps associated with data stored in the biological sensor 102 to time stamps associated with data stored in the databases 306 of the sensor management system 304 (or the memory of the computing device 202). If the time stamps of the sensor management system 304 (or the memory of the computing device 202) are not the same as the time stamps of the biological sensor 102, then the sensor management system 304 (or the computing device 202) can detect the biological sensor 102 has not been provisioned. In yet another embodiment, the biological sensor 102 can provide the sensor management system 304 (or the computing device 202) information indicating it has not been provisioned.

These and other alternative embodiments for determining whether a biological sensor 102 is provisioned are contemplated by the subject disclosure.

Referring back to step 606, if the sensor management system 304 (or the computing device 202) detects the biological sensor 102 is not provisioned, the sensor management system 304 (or the computing device 202) can proceed to step 608 where it can determine whether historical sensor data is available. The historical sensor data can originate from prior biological sensors used by the patient 100. The historical sensor data can represent data captured minutes, hours, days, months or years before the new biological sensor 102 is detected at step 604. If the historical sensor data is available, the sensor management system 304 (or the computing device 202) can proceed to step 610 to obtain such data from a memory device used to retain records of the patient 100 (e.g., the customer sensor databases 306 or an internal memory of the computing device 202).

Once the historical sensor data is obtained, the sensor management system 304 (or the computing device 202) can proceed to step 614 to determine normative conditions and/or thresholds for detecting one or more biological conditions of the patient 100 from the historical sensor data collected from one or more previously used biological sensors 102. The historical sensor data collected from the one or more previously used biological sensors 102 can be over a period of time such as minutes, hours, days, weeks, months, years, or longer. The time period used for selecting historical sensor data can be driven by a number of factors. For example, the time period may be based on a specific protocol initiated by a clinician (nurse and/or doctor). The protocol can be initiated as a result of a procedure performed on the patient (e.g., surgery, therapy, drug application, and so on), a protocol for monitoring patient vitals, or a protocol customized by the clinician to address a particular disease. Any medical protocol prescribed by the clinician or a medical organization are contemplated by the subject disclosure. Once a time period is selected, the historical sensor data can be analyzed to identify one or more normative conditions and/or thresholds for the patient 100. FIGS. 7A-7D illustrate non-limiting example embodiments for determining normative conditions, and thresholds for detecting biological conditions.

Figure 7A:
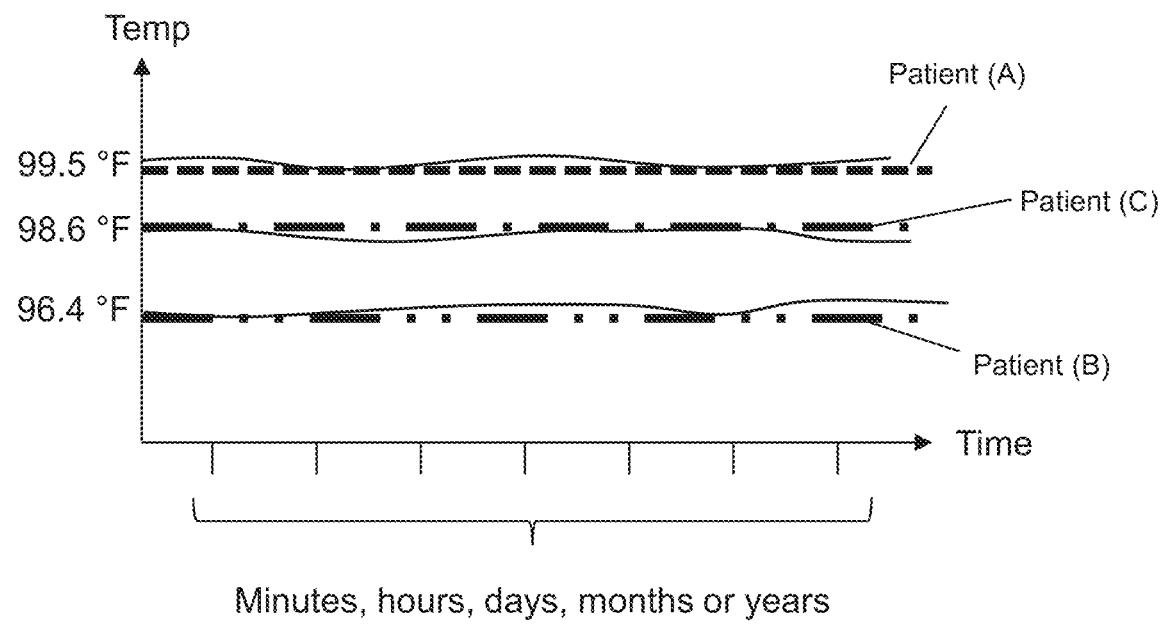
FIGS. 7A-7B are block diagrams illustrating example, non-limiting embodiments of plots of sensor data of a plurality of patients in accordance with various aspects of the subject disclosure described herein.

Turning now to FIG. 7A, a block diagram illustrating an example, non-limiting embodiment of a plot of sensor data of a plurality of patients in accordance with various aspects of the subject disclosure is shown. FIG. 7 depicts three patients (A), (B) and (C). Historical sensor data of patient (A) indicates that the patient has had an average temperature of 99.5° Fahrenheit (F) over a select period. In one embodiment, the clinician may be aware that patient (A) has exhibited this temperature over extended periods of time and thereby can form an opinion that such a temperature does not pose a health risk to patient (A) even though it is higher than a population norm of 98.6° F. In one embodiment, the clinician can record his opinion in a chart of patient (A), which can be accessible to the sensor management system 304 (or the computing device 202). In one embodiment, the sensor management system 304 (or the computing device 202) can access the chart of patient (A) and determine from the clinician's opinion that such a temperature may be considered a normative condition for patient (A) given the physiological state and health of patient (A). In another embodiment, the sensor management system 304 (or the computing device 202) can analyze the sensor data of the patient (A) in relation to the patient's temperature, other sensory data (e.g., blood pressure, pulse rate, respiration rate, blood pressure and so on) and/or other medical history, and determine, without relying on the clinician's opinion, that such a temperature may be considered a normative condition for patient (A) given the physiological state and health of patient (A).

In another embodiment, the clinician may be aware that patient (A) may be subject to an illness that the clinician expects will result in a rise in temperature, which the clinician records in the chart of patient (A). In yet another embodiment, the clinician may be applying a drug treatment to patient (A) that the clinician knows will cause a rise in temperature, which the clinician records in the chart of patient (A). The sensor management system 304 (or the computing device 202) can be configured to analyze the chart of patient (A) and consider the temperature a normative condition of patient (A) based on the entries of the clinician indicating an expected rise in temperature. Alternatively, the sensor management system 304 (or the computing device 202) can be configured to analyze the sensor data, detect from the chart that patient (A) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the temperature of patient (A) would be higher than normal, and therefore can be considered a normative condition of patient (A).

Turning now to patient (B), the historical sensor data of patient (B) indicates that the patient has had an average temperature of 96.4° F. over a select period. In one embodiment, the clinician may be aware that patient (B) has exhibited this temperature over extended periods of time and that such a temperature does not pose a health risk to patient (B). Clinician can record his or her opinion in a chart of patient (B) accessible to the sensor management system 304 (or the computing device 202). Thus such a temperature may be considered a normative condition for patient (B) given the physiological state and health of patient (B). In another embodiment, the clinician may be aware that patient (B) may be subject to an illness that results in such a temperature. In yet another embodiment, the clinician may be applying a drug treatment to patient (B) that the clinician knows will cause a drop in temperature.

The sensor management system 304 (or the computing device 202) can be configured to analyze the chart of patient (B) and consider the temperature a normative condition of patient (B) based on the entries of the clinician indicating an expected drop in temperature. Alternatively, the sensor management system 304 (or the computing device 202) can be configured to analyze the sensor data, detect from the chart that patient (B) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the temperature of patient (B) would be lower than normal, and therefore can consider it a normative condition of patient (B).

Turning now to patient (C), the historical sensor data of patient (C) indicates that the patient has had an average temperature of 98.6° F. over a select period, which coincides with what most clinicians may consider an average temperature for the general population. Thus the clinician does not have to consider exceptions for patient (C). Accordingly, this temperature will be used as a normative condition for patient (C). The sensor management system 304 (or the computing device 202) can be configured to analyze the chart of patient (C) and consider the temperature a normative condition of patient (C). Alternatively, the sensor management system 304 (or the computing device 202) can be configured to analyze the sensor data, and determine, without relying on the clinician's opinion, that the sensor data coincides with the general population, and therefore can consider it a normative condition of patient (C).

Figure 7B:
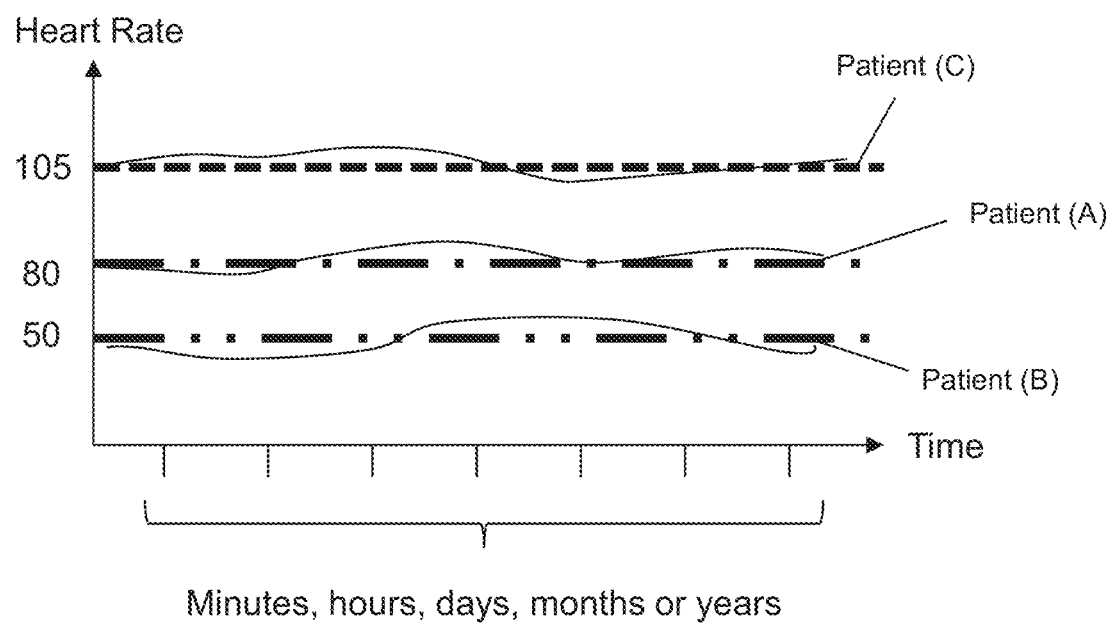

Turning now to FIG. 7B, a block diagram illustrating an example, non-limiting embodiment of a plot of sensor data of the plurality of patients (A)-(C) of FIG. 7A. Historical sensor data of patient (A) indicates that the patient has had an average pulse rate of 80 beats per minute over a select period. The sensor management system 304 (or the computing device 202) can be configured to consider such a pulse rate a normative condition for patient (A) given that a range of 60 to 100 beats per minute is generally a healthy pulse rate. In one embodiment, the clinician can record his opinion in a chart of patient (A), which can be accessed by the sensor management system 304 (or the computing device 202).

Turning now to patient (B), the historical sensor data of patient (B) indicates that the patient has had an average pulse rate of 50 beats per minute over a select period. In one embodiment, the clinician may be aware that patient (B) has exhibited this pulse rate over extended periods of time given the athletic training undertaken by patient (B). In one embodiment, the clinician can record his opinion in a chart of patient (B), which can be accessed by the sensor management system 304 (or the computing device 202). In one embodiment, the sensor management system 304 (or the computing device 202) can access the chart of patient (B) and determine from the clinician's opinion that such a pulse rate may be considered a normative condition for patient (B) given the physiological state and health of patient (B). In another embodiment, the sensor management system 304 (or the computing device 202) can analyze the sensor data of the patient (B) in relation to the patient's pulse rate, other sensory data (e.g., temperature, blood pressure, respiration rate, blood pressure and so on) and other medical history, and determine, without relying on the clinician's opinion, that such a pulse rate may be considered a normative condition for patient (B) given the physiological state and health of patient (B).

Turning now to patient (C), the historical sensor data of patient (C) indicates that the patient has had an average pulse rate of 105 beats per minute over a select period, which is above normal. In one embodiment, the clinician may be aware that patient (C) has a condition such as, for example, hypertension, coronary artery disease, thyroid disease, etc., which can result in a higher pulse rate that the clinician records in the chart of patient (C). In yet another embodiment, the clinician may be applying a drug treatment to patient (C) that the clinician knows will cause a rise in pulse rate, which the clinician records in the chart of patient (C).

In one embodiment, the sensor management system 304 (or the computing device 202) can be configured to analyze the chart of patient (C) and consider the pulse rate a normative condition of patient (C) based on the entries of the clinician indicating an expected rise in pulse rate. Alternatively, the sensor management system 304 (or the computing device 202) can be configured to analyze the sensor data, detect from the chart that patient (C) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the pulse rate of patient (C) would be higher than normal, and therefore can be considered a normative condition of patient (C).

Figure 7C:
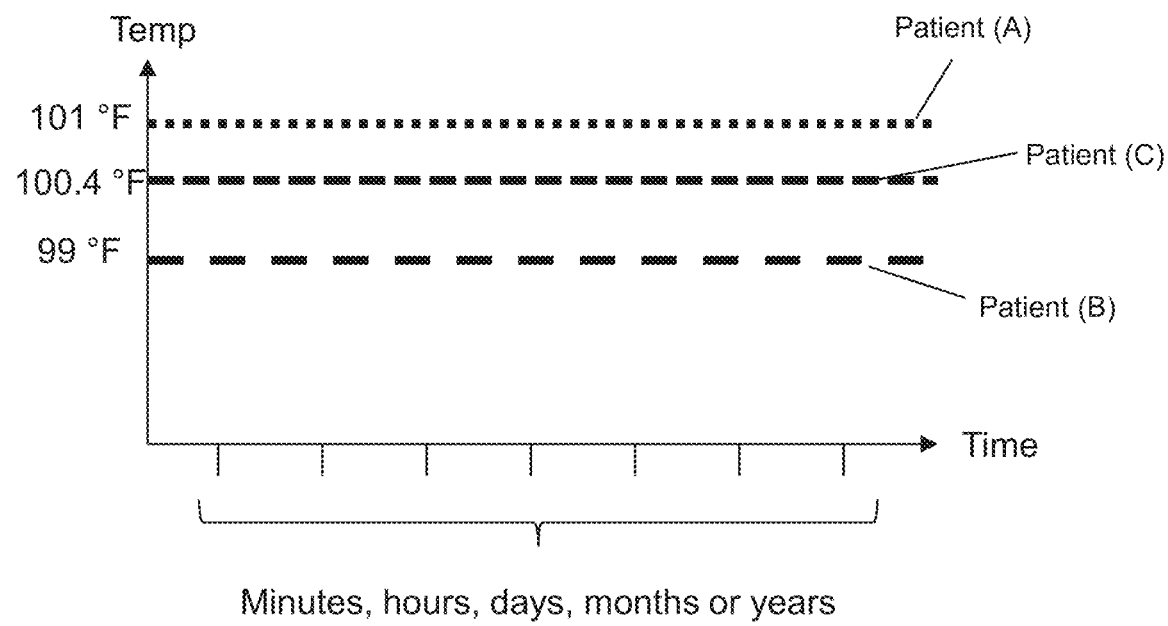
FIGS. 7C-7D are block diagrams illustrating example, non-limiting embodiments of thresholds used for monitoring biological conditions of the plurality of patients of FIGS. 7A-7B in accordance with various aspects of the subject disclosure described herein.

Turning now to FIG. 7C, a block diagram illustrating an example, non-limiting embodiment of temperature thresholds used for monitoring biological conditions of the plurality of patients (A)-(C) according to the sensor data of FIG. 7A. Turning now to patient A, given the normative condition of patient (A) averages at 99.5° F., the clinician may consider an adverse biological condition to begin at 101° F. If, for example, patient (A) does not have an illness or is not being treated with drug therapy to cause a normative condition at 99.5° F., then a threshold of 101° F. may be considered the beginning of a fever. If, on the other hand, patient (A) is subject to an illness or drug therapy resulting in the normative condition, then a rise in temperature to 101° F. may reflect an adverse biological condition that is more than just a fever. For example, the adverse biological condition may represent a body's negative reaction to the drug therapy and/or a worsening of the illness. In one embodiment, the threshold can be established by the clinician, which the clinician can record in the chart of patient (A). In another embodiment the threshold can be established by protocols relating to the illness and/or the drug therapy.

In one embodiment, the sensor management system 304 (or the computing device 202) can be configured to analyze the chart of patient (A) and generate the threshold shown in FIG. 7C. Alternatively, the sensor management system 304 (or the computing device 202) can be configured to analyze the normative condition of patient (A), detect from the chart that patient (A) has an illness, and/or is subject to a drug therapy, access information relating to the illness and/or drug therapy (e.g., specific protocols), and determine, without relying on the clinician's proposed threshold, the threshold shown in FIG. 7C.

Turning now to patient (B), given the normative condition of patient (B) averages at 96.4° F., the clinician may consider an adverse biological condition to begin at 99° F. If, for example, patient (B) does not have an illness or is not being treated with drug therapy to cause a normative condition at 96.4° F., then a threshold of 99° F. may be considered the beginning of a fever. If, on the other hand, patient (B) is subject to an illness or drug therapy resulting in the normative condition, then a rise in temperature to 99° F. may reflect an adverse biological condition that is more than just a fever. For example, the adverse biological condition may represent a body's negative reaction to the drug therapy and/or a worsening of the illness. In one embodiment, the threshold can be established by the clinician, which the clinician can record in the chart of patient (B). In another embodiment the threshold can be established by protocols relating to the illness and/or the drug therapy.

In one embodiment, the sensor management system 304 (or the computing device 202) can be configured to analyze the chart of patient (B) and generate the threshold shown in FIG. 7C. Alternatively, the sensor management system 304 (or the computing device 202) can be configured to analyze the normative condition of patient (B), detect from the chart that patient (B) has an illness, and/or is subject to a drug therapy, access information relating to the illness and/or drug therapy (e.g., specific protocols), and determine, without relying on the clinician's proposed threshold, the threshold shown in FIG. 7C.

Turning now to patient (C), given the normative condition of patient (C) averages at 98.6° F. is considered normal for the general population, the clinician may consider an adverse biological condition to begin at 100.4° F. Such a threshold can be used for detecting a fever. The clinician can record in the chart of patient (C) that patient (C) exhibits the temperature norm of the general population. The sensor management system 304 (or the computing device 202) can be configured to analyze the chart of patient (C) and generate the threshold shown in FIG. 7C. Alternatively, the sensor management system 304 (or the computing device 202) can be configured to analyze the normative condition of patient (C), and determine that an appropriate threshold for detecting a fever follows the norm of the general population and thus arrive at the threshold shown in FIG. 7C.

Figure 7D:
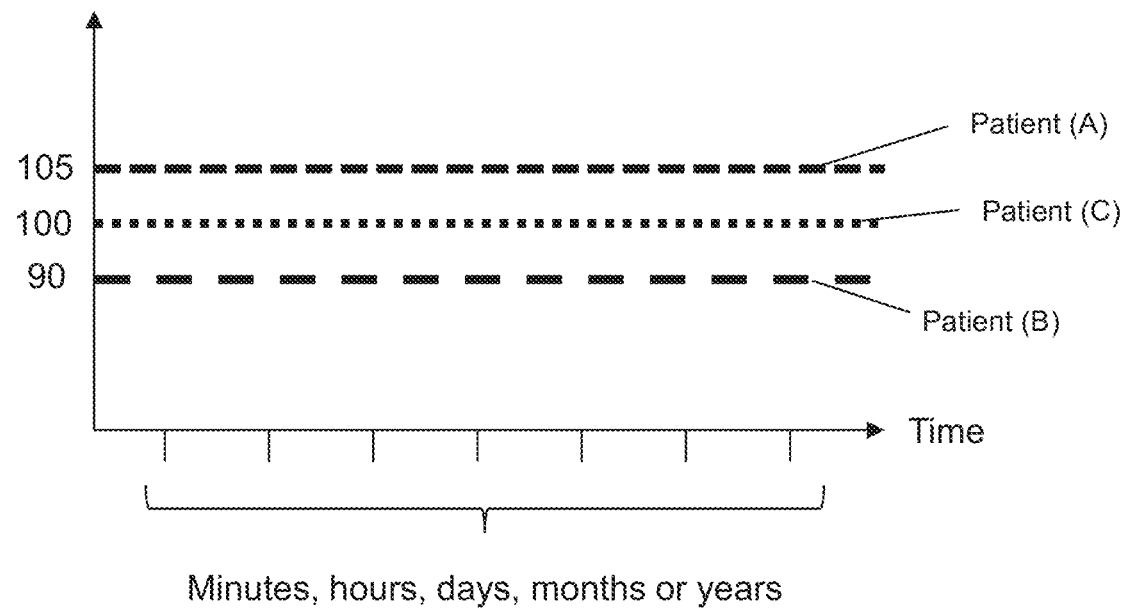

Turning now to FIG. 7D, a block diagram illustrating an example, non-limiting embodiment of pulse rate thresholds used for monitoring biological conditions of the plurality of patients (A)-(C) according to the sensor data of FIG. 7B. Turning now to patient A, given the normative condition of patient (A) averages at 80 beats per minute, which is considered normal for the general population, the clinician may consider an adverse biological condition to begin at 105 beats per minute when the patient is at rest (5% above the norm of the general population, which is 100 beats per minute). The biological sensor 102 used by patient (A) can detect that the patient is at rest utilizing, for example, the motion sensor 418 depicted in FIG. 4. In one embodiment, the threshold can be established by the clinician, which the clinician can record in the chart of patient (A). In one embodiment, the sensor management system 304 (or the computing device 202) can be configured to analyze the chart of patient (A) and generate the threshold shown in FIG. 7D. Alternatively, the sensor management system 304 (or the computing device 202) can be configured to analyze the normative condition of patient (A), and determine, without relying on the clinician's opinion, that patient (A) should use a threshold applied to the general population, such as, for example, a threshold of 100 beats per minute.

Turning now to patient (B), given the normative condition of patient (B) averages at 50 beats per minute, if, for example, patient (B) does not have an illness and is not being treated with drug therapy to cause a normative condition at 50 beats per minute, then the clinician may consider an adverse biological condition to begin at 90 beats per minute when the patient is at rest. Even though 90 beats per minute is below a population threshold of 100 beats per minute, the clinician may consider a change from 50 to 90 beats per minute to be a substantial change for a patient with a history of rigorous athletic training. The biological sensor 102 used by patient (B) can detect that the patient is at rest utilizing, for example, the motion sensor 418 depicted in FIG. 4. The chart of patient (B) may also include information indicating the last time patient (B) was measured at 50 beats per minute.

In one embodiment, the sensor management system 304 (or the computing device 202) can be configured to determine from the chart of patient (B) the threshold of 90 beats per minute and thereafter monitor patient (B) for unexpected changes. The sensor management system 304 (or the computing device 202) can also be configured to detect unexpected rapid changes in pulse rate in a relatively short period (e.g., 48 hours or less). Further, the sensor management system 304 (or the computing device 202) can also be configured to detect a trend in the pulse rate of patient (B) (e.g., an upward trend in pulse rate over weeks or months).

Turning now to patient (C), given the normative condition of patient (C) averages at 105 beats per minute, which is high (likely due to illness, e.g., hypertension), the clinician may consider an adverse biological condition to begin at 100 beats per minute when patient (C) is at rest. The clinician may have set a threshold below the normative condition as a result of the clinician prescribing medication to reduce hypertension in patient 100. Such prescription may reduce the pulse rate of the patient by, for example, 15% (e.g., ~90 beats per minute). The clinician can enter the prescribed medication in the chart of patient 100 which is accessible to the sensor management system 304 (or the computing device 202). Although FIG. 7B shows a normative condition of 105 beats per minute, the sensor management system 304 (or the computing device 202) can be configured to recognize an adjusted normative condition of 90 beats per minute while patient 100 is using the hypertension medication.

In one embodiment, the sensor management system 304 (or the computing device 202) can be configured to determine from the chart of patient (C) the threshold of 100 beats per minute and thereafter monitor patient (C) for unexpected changes. The sensor management system 304 (or the computing device 202) can also be configured to detect unexpected rapid changes in pulse rate in a relatively short period (e.g., 48 hours or less). Further, the sensor management system 304 (or the computing device 202) can also be configured to detect a trend in the pulse rate of patient (C) (e.g., an upward trend in pulse rate over weeks or months).

The foregoing embodiments for determining normative conditions and thresholds of a patient as shown in FIGS. 7A-7D can also be used for other vital signs (e.g., blood pressure, respiration rate), as well as to other biological functions that can be measured for a patient (e.g., red cell count, SpO2, glucose levels in the blood, electrocardiogram measurements, and so on). Additionally, the sensor management system 304 (or the computing device 202) can be configured to analyze sensor data of more than one biological function at a time to assess normative conditions and thresholds rather than relying on a single biological function. The sensor management system 304 (or the computing device 202) can, for example, correlate one type of biological sensor data (e.g., pulse rate) with another type of biological sensor data (e.g., blood pressure) to determine a normative condition and/or threshold. In this manner, the sensor management system 304 (or the computing device 202) can perform a more holistic analysis of the patient's sensor data.

It is further noted that the normative conditions and the thresholds of FIGS. 7A-7D can have a temporal component. That is, a normative condition may be considered normative only for a period of time either by instructions from the clinician, medical protocols and/or other medical conditions associated with the patient 100 that can be determined by the sensor management system 304 (or the computing device 202). In one embodiment, a threshold can be set for a specific time period. For example, the sensor management system 304 (or the computing device 202) can detect when a drug therapy has begun and when it ends by obtaining information from the chart of the patient 100. In an embodiment, the sensor management system 304 (or the computing device 202) can be configured to change normative conditions and corresponding thresholds upon expiration of such periods.

In another embodiment, the sensor management system 304 (or the computing device 202) can be adapted to use ranges of the normative conditions and thresholds shown in FIGS. 7A-7D. That is, a normative condition and/or a threshold can have a range having an upper and lower limit. In another embodiment, more than one normative condition and more than one threshold can be used to identify different biological conditions that may arise in a patient as the patient's sensor data shows measurements drifting in one direction or another. In yet another embodiment, the sensor management system 304 (or the computing device 202) can be adapted to detect sensor data trends that it can use to predict future outcomes before they occur. A sensor data trend can, for example, identify a specific course that measurements may be taking, which in turn can provide the sensor management system 304 (or the computing device 202) a projected trajectory and time when an adverse condition may occur. In another embodiment, the sensor management system 304 (or the computing device 202) can be adapted to detect erratic changes in sensor data. Such changes can be flagged as a problem with the biological sensors 102 (e.g., a malfunction) and/or biological issues that may need to be addressed.

It is further noted that algorithms for detecting biological conditions can be generated by the sensor management system 304 (or the computing device 202). In one embodiment, for example, the sensor management system 304 (or the computing device 202) can be configured to generate a script or software program that emulates a specific medical protocol used for detecting biological conditions associated with an illness of the patient, an adverse reaction to a drug therapy being applied to the patient, or some other biological condition to be monitored. The script or software can be generated by the sensor management system 304 (or the computing device 202) can, for example, detect trends, detect when sensor measurements exceed thresholds, detect erratic or rapid changes, applying hysteresis to sensor measurements to filter out short bursts of anomalous readings, detect malfunctions in the biological sensor 102, and so on. So long as the biological sensor 102 has the computing resources, any algorithm of any complexity can be supplied to the biological sensor 102. For example, a script or software can determine how often a patient 100 is sensed. Patients that are healthy, for instance, may be sensed less frequently thereby saving battery power of the sensor 102. Patients that may have a condition may have a script or software that's more aggressive on readings.

The script or software can comprise instructions executable by the biological sensor 102, or macro instructions that can be translated (compiled) by the biological sensor 102 into executable instructions. Each algorithm can be given a version which can be sent to the biological sensors 102 for version tracking. As medical protocols change, the sensor management system 304 (or the computing device 202) can query biological sensors 102 for versions and download new algorithmic versions when a version used by the biological sensors 102 is out-of-date. The sensor management system 304 (or the computing device 202) can also be configured to provide new algorithmic versions to the biological sensors 102 that are pre-programmed with a certain algorithmic version that may be out-of-date.

Referring back to FIG. 6, the foregoing embodiments illustrate ways to process historical sensor data obtained at step 610 (and chart information if available for the patient 100) to determine normative conditions and/or thresholds at step 614. It is noted that chart information may be electronically stored by the sensor management system 304, the computing device 202, or other storage systems accessible by the sensor management system 304 and/or the computing device 202.

Referring back to step 608, if the sensor management system 304 (or the computing device 202) detects that historical sensor data is not available for the patient 100, the sensor management system 304 (or the computing device 202) can proceed to step 612. At this step, the sensor management system 304 (or the computing device 202) can collect sensor data from the new sensor until sufficient sensor data is available to determine normative conditions and/or thresholds for the patient according to the sensor data (and chart information if available for the patient).

Referring now to step 614, once the normative condition(s) and/or threshold(s) have been determined according to historical sensor data obtained at step 610, the sensor management system 304 (or the computing device 202) can proceed to step 616 and generate provisioning information for the new biological sensor 102 detected at step 606. The provisioning information can include, among other things, one or more normative conditions, one or more thresholds, one or more algorithms (if the biological sensor 102 is not pre-programmed or has an out-of-date algorithm), a most recent history of sensor data measurements (e.g., measurements performed in the last hour), identification information of the patient 100, a last known location of the patient, certain chart information relating to the patient (e.g., illness type, drug therapy type, date of surgery, type of surgery, etc.), and so on. The amount of information included in the provisioning information generated at step 616 can depend on the memory resources of the biological sensor 102, the function of the biological sensor 102, usage preferences of the clinician (e.g., ability to recall a short history of sensor data), and so forth.

Once provisioning information has been generated, the sensor management system 304 (or the computing device 202) can proceed to step 618 and provide the provisioning information to the biological sensor 102. The biological sensor 102 can then begin to monitor one or more biological conditions of the patient at step 620. Such conditions can be determined from an algorithm provided to (or pre-programmed in) the biological sensor 102. In one embodiment, the algorithm can detect that sensor measurements exceed a specific threshold or a threshold range. In other embodiments, the algorithm can detect sensor data trends, erratic or rapid changes, and/or predict future outcomes. At step 622, the biological sensor 102 can provide the sensor management system 304 (or the computing device 202) information relating to detection of biological conditions monitored by the biological sensor 102, including without limitations, sensor data measurements, measurements exceeding a specific threshold or threshold range, trends in sensor data, erratic or rapid changes in sensor data, predicted adverse biological conditions, and so on. Such information can be provided to the sensor management system 304 (or the computing device 202) with time stamps (e.g., time of day: hours/minutes/second, date: month/day/year).

If trend information is not provided at step 622, the sensor management system 304 (or the computing device 202) can be configured at step 624 to analyze the sensor data to detect trends, erratic or rapid changes and so on. The sensor management system 304 (or the computing device 202) can also be configured to report a status of biological conditions of the patient 100 to clinicians. For example, if no adverse biological conditions have been detected, the clinician can be provided a history of the measured sensor data in a status report that indicates no adverse biological conditions were detected. If, on the other hand, one or more adverse biological conditions were detected, the clinician can be provided with a detailed report that includes sensor data that exceeded one or more thresholds, time stamp information associated with the sensor data, and so on. The sensor management system 304 (or the computing device 202) can also be configured to provide trend information if available. If adverse biological conditions are not presently detected, but trend information predicts a future adverse condition, then the sensor management system 304 (or the computing device 202) can provide such information to the clinician to enable the clinician to take preemptive action to avoid such adverse condition from occurring.

At steps 626-628, the sensor management system 304 (or the computing device 202) can monitor placement of another new biological sensor 102 on the patient 100. If another new biological sensor 102 is not detected, the sensor management system 304 (or the computing device 202) can proceed to step 620 and repeat the processes previously described. If, however, another new biological sensor 102 is detected, the sensor management system 304 (or the computing device 202) can proceed to step 628 to obtain a model number, serial number or other identification data from the new biological sensor 102 to determine if the new sensor is of the same type and function as the previous sensor. Additionally, the sensor management system 304 (or the computing device 202) can obtain patient identification data from the new biological sensor 102, which the biological sensor may have obtained from a wrist band of the patient including an RFID, the biometric sensor 409 of FIG. 4, or by patient information provided to the biological sensor 102 by way of the computing device 202 of the clinician as depicted in FIG. 2B.

If the new biological sensor 102 is the same as the previous sensor and has been coupled to the same patient, then the sensor management system 304 (or the computing device 202) can proceed to step 630 and determine if the new biological sensor 102 is a replacement for the previous same sensor. If the new biological sensor 102 is not the same as the previous sensor, a determination can be made whether the new sensor is a replacement sensor by the sensor management system 304 (or the computing device 202) by obtaining information from the new sensor indicating it is a replacement sensor, determining that the new sensor does have in its memory a patient identifier, or by receiving input data from, for example, the computing device 202 initiated by, for example, a clinician, indicating it is a replacement sensor. If such information is not provided by the new sensor or the computing device 202, and/or the new sensor has been coupled to a different patient, then the sensor management system 304 (or the computing device 202) can proceed to step 606 and perform the same sequence of steps previously described for the same patient if the new sensor is associated with the same patient, or for a different patient in which case a new record would be created in the databases 306 or other storage resources of the sensor management system 304 (or the computing device 202).

Referring back to step 630, in one embodiment, the sensor management system 304 (or the computing device 202) can determine that the new biological sensor 102 is replacing the previous sensor upon receiving a message from the computing device 202 of the clinician as noted above. The message can indicate which sensor is being replaced by identifying the serial number of the previous sensor in the message and identifying the serial number of the new sensor. In another embodiment, the sensor management system 304 (or the computing device 202) can determine that the new biological sensor 102 is replacing a previous sensor based on the new biological sensor 102 not being programmed with a patient identifier. In yet another embodiment, the sensor management system 304 (or the computing device 202) can determine that the new biological sensor 102 is replacing a previous sensor based on an understanding that two of the same type of sensors for the same patient is not common practice for the clinician and in such instances detecting a new sensor represents a replacement procedure undertaken by the clinician. It should be noted that there may be instances when a new biological sensor of the same type will not be considered a replacement sensor. For example, a clinician may wish to use the same sensor in multiple locations of a patient's body. Such exceptions can be noted by the clinician using the computing device 202. In yet another embodiment, the sensor management system 304 (or the computing device 202) can determine that the new biological sensor 102 is replacing a previous sensor based on a utilization period of the previous sensor expiring or detecting that the previous sensor is damaged or malfunctioning. Other suitable detection methods for determining a replacement of sensors are contemplated by the subject disclosure.

Once a replacement event is detected, the sensor management system 304 (or the computing device 202) can proceed to step 634 and decommission the previous sensor. The decommissioning process can represent noting in a record of the patient 100 that the serial number of the biological sensor 102 being replaced has been decommissioned. Once the sensor is decommissioned, the sensor management system 304 (or the computing device 202) can be configured to ignore sensor data from the decommissioned sensor if such data were to be provided. The sensor management system 304 (or the computing device 202) can then proceed to step 610 to obtain historical sensor data produced by the previous sensor and any predecessor sensors. The sensor management system 304 (or the computing device 202) can then proceed to perform subsequent steps as previously described. The sensor management system 304 (or the computing device 202) can be provisioned to provide the new biological sensor 102 some or all of the obtained historical sensor data of one or more previous sensors for local storage, enabling retrieval by the computing device 202 if desired. It is further noted that the steps of method 600 can be adapted so that the sensors 102 (new or old) can proactively (e.g., without polling by the sensor management system 304 or the computing device 202) initiate communications with the sensor management system 304 or the computing device 202 and provide updates as needed. Such a process can be pre-programmed into the sensors 102 or a script or software can be provided to the sensors 102 by the sensor management system 304 or the computing device 202 to enable a proactive communication process.

While for purposes of simplicity of explanation, the respective processes are shown and described as a series of blocks in FIG. 6, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Upon reviewing the aforementioned embodiments, it would be evident to an artisan with ordinary skill in the art that said embodiments can be modified, reduced, or enhanced without departing from the scope of the claims described below. For example, method 600 can be adapted so that the sensor management system 304 or the computing device 202 tracks GPS coordinates of patients 100 using a location receiver 416 of the biological sensor 102. GPS data can be used, for example, to analyze the activities of the patient 100 and in some instances such activities may be used to analyze the sensor data. For example, the GPS coordinate data may indicate that a patient was walking or jogging. Such information can be used to distinguish sensor data taken at rest versus other activities. Orientation and motion data produced by the orientation sensor 420 and motion sensor 418 can be used to more accurately assess a 3D position of the patient 100, and a level of activity of the patient 100 (e.g., lying down, running in place, sitting, etc.). By further refining the activity of the patient 100 with 3D positioning information, the sensor management system 304 can more precisely analyze sensor data obtained from one or more biological sensors 102 coupled to a patient 100.

It should be understood that devices described in the exemplary embodiments can be in communication with each other via various wireless and/or wired methodologies. The methodologies can be links that are described as coupled, connected and so forth, which can include unidirectional and/or bidirectional communication over wireless paths and/or wired paths that utilize one or more of various protocols or methodologies, where the coupling and/or connection can be direct (e.g., no intervening processing device) and/or indirect (e.g., an intermediary processing device such as a router).

Figure 8:
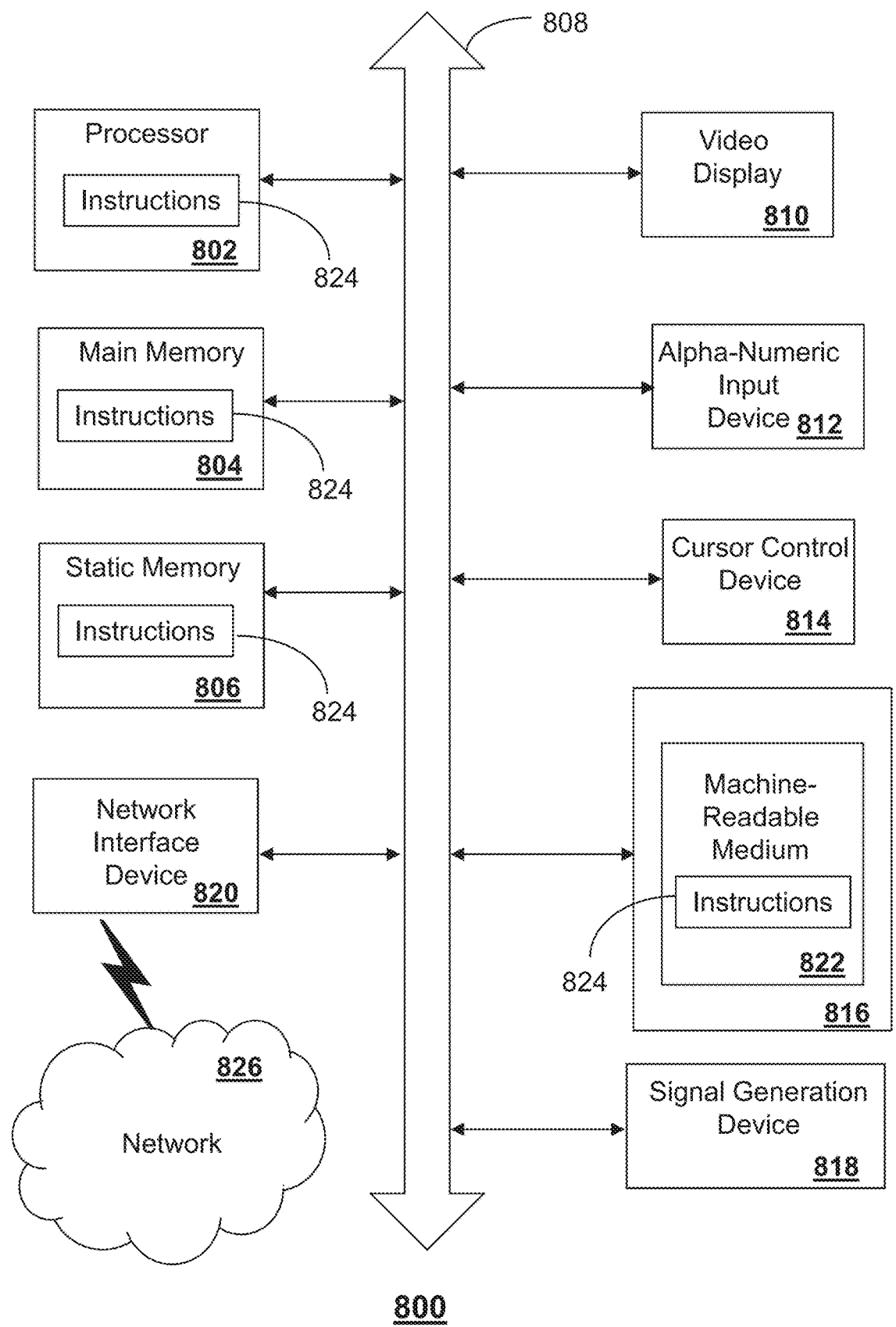
FIG. 8 is a diagrammatic representation of a machine in the form of a computer system within which a set of instructions, when executed, may cause the machine to perform any one or more of the methods of the subject disclosure described herein.

FIG. 8 depicts an exemplary diagrammatic representation of a machine in the form of a computer system 800 within which a set of instructions, when executed, may cause the machine to perform any one or more of the methods described above. One or more instances of the machine can operate, for example, as the devices depicted in the drawings of the subject disclosure. In some embodiments, the machine may be connected (e.g., using a network 826) to other machines. In a networked deployment, the machine may operate in the capacity of a server or a client user machine in a server-client user network environment, or as a peer machine in a peer-to-peer (or distributed) network environment.

The machine may comprise a server computer, a client user computer, a personal computer (PC), a tablet, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 800 may include a processor (or controller) 802 (e.g., a central processing unit (CPU)), a graphics processing unit (GPU, or both), a main memory 804 and a static memory 806, which communicate with each other via a bus 808. The computer system 800 may further include a display unit 810 (e.g., a liquid crystal display (LCD), a flat panel, or a solid state display). The computer system 800 may include an input device 812 (e.g., a keyboard), a cursor control device 814 (e.g., a mouse), a disk drive unit 816, a signal generation device 818 (e.g., a speaker or remote control) and a network interface device 820. In distributed environments, the embodiments described in the subject disclosure can be adapted to utilize multiple display units 810 controlled by two or more computer systems 800. In this configuration, presentations described by the subject disclosure may in part be shown in a first of the display units 810, while the remaining portion is presented in a second of the display units 810.

The disk drive unit 816 may include a tangible computer-readable storage medium 822 on which is stored one or more sets of instructions (e.g., software 824) embodying any one or more of the methods or functions described herein, including those methods illustrated above. The instructions 824 may also reside, completely or at least partially, within the main memory 804, the static memory 806, and/or within the processor 802 during execution thereof by the computer system 800. The main memory 804 and the processor 802 also may constitute tangible computer-readable storage media.

Dedicated hardware implementations including, but not limited to, application specific integrated circuits, programmable logic arrays and other hardware devices can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 822 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure. The term "non-transitory" as in a non-transitory computer-readable storage includes without limitation memories, drives, devices and anything tangible but not a signal per se.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth®, WiFi, Zigbee®), and long-range communications (e.g., WiMAX, GSM, CDMA, LTE) can be used by computer system 800.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A system, comprising:
a processor; and
a memory that stores executable instructions that, when executed by the processor, facilitate performance of operations, comprising:
  receiving, from a first sensor adapted to be coupled to a first patient, first sensor data comprising biological data of the first patient;
  storing the first sensor data in an information storage system;
  receiving, from a second sensor different than the first sensor, a communication;
  determining that the first sensor is being replaced by the second sensor by:
    determining, based on the communication from the second sensor, an identifier of the second sensor;
    identifying the first patient;
    retrieving a record associated with the first patient; and
    determining that the identifier of the second sensor is omitted from the record;
  based on determining that the first sensor is being replaced by the second sensor:
    accessing, in the information storage system, the first sensor data;
    accessing, in the information storage system, a protocol related to at least one of an illness experienced by the first patient or a therapy administered to the first patient;
    generating, according to the first sensor data and the protocol, a threshold to detect a biological condition of the first patient, the illness being different than the biological condition; and
    transmitting the threshold to the second sensor.

2. The system of claim 1, wherein the operations further comprise:
determining, according to the first sensor data, at least one of a patient identifier to identify the first patient or a room identifier to locate a room used by the first patient.

3. The system of claim 1, wherein the threshold is a first threshold and the operations further comprise:
receiving third sensor data from a third sensor adapted to be coupled to a second patient;
generating, according to the third sensor data, a second threshold to detect the biological condition of the second patient; and
transmitting the second threshold to the third sensor for detecting the biological condition in the second patient, wherein the second patient differs from the first patient, and wherein the second threshold differs from the first threshold.

4. The system of claim 1, wherein the determining that the first sensor is being replaced by the second sensor comprises receiving a signal from a computing device indicating that the first sensor is being replaced by the second sensor or receiving data from the second sensor indicating the second sensor has not been provisioned.

5. The system of claim 1, wherein the determining that the first sensor is being replaced by the second sensor further comprises detecting that a utilization period of the first sensor has expired or the first sensor is damaged.

6. The system of claim 1, wherein the memory further stores first time stamps, and
  wherein the determining that the first sensor is being replaced by the second sensor further comprises determining that the first time stamps are different than second time stamps associated with the second sensor.

7. The system of claim 1, further comprising:
a portable communication device or an immobile communication device, wherein the portable communication device or the immobile communication device is communicatively coupled to the first sensor or the second sensor, and wherein the portable communication device or the immobile communication device is located in a vicinity of the first sensor or the second sensor.

8. The system of claim 1, wherein the system comprises a server, and wherein the server is communicatively coupled to the first sensor or the second sensor via a wireless gateway located in a vicinity of the first sensor or the second sensor.

9. The system of claim 1, wherein the threshold is a first threshold, and the operations further comprise:
identifying, in a record associated with the first patient, a second threshold to detect the biological condition, the second threshold being proposed by a clinician, and
wherein the first threshold is determined without relying on the second threshold.

10. The system of claim 9, wherein the first threshold is generated based on an average of measurements in the first sensor data.

11. The system of claim 1, further comprising:
a wristband including a Radio Frequency Identification (RFID) device configured to transmit an identification of the first patient to the second sensor; and
the second sensor configured to receive the identification of the first patient from the RFID device and to transmit the identification of the first patient in the communication,
wherein the operations further comprise recording, in the record, the identification of the second sensor, and
wherein the first sensor and the second sensor are a same type of sensor.

12. The system of claim 1, wherein the operations further comprise:
storing, in the information storage system, an indication that the first sensor has been decommissioned, the indication comprising a serial number of the first sensor;
based on storing the indication:
  receiving, from the first sensor, third sensor data; and
  ignoring the third sensor data by refraining from storing the third sensor data in the information storage system;

receiving, from the second sensor, second sensor data indicating that the biological condition of the first patient has been detected based on the threshold; and
storing, in the information storage system, the second sensor data.

13. A non-transitory machine-readable storage medium, comprising executable instructions that, when executed by a processor, facilitate performance of operations, comprising:
receiving a communication from a first sensor adapted to be removably coupled to a skin surface of a patient;
determining that the first sensor is replacing a second sensor currently removably coupled to the skin surface of the patient by:
determining, based on the communication from the first sensor, an identifier of the first sensor;
identifying the patient;
retrieving a record associated with the patient; and
determining that the identifier of the first sensor is omitted from the record associated with the patient;
based on determining that the first sensor is replacing the second sensor:
determining, from sensor data collected by the second sensor for the patient over a period of time, a normative condition of a biological function of the patient;
accessing, in an information storage system, a protocol related to at least one of an illness experienced by the patient or a therapy administered to the patient, the illness being different than an abnormal state of the biological function;
generating, according to the normative condition and the protocol, a threshold to detect the biological function of the patient; and
transmitting the threshold to the first sensor to enable the first sensor to detect the abnormal state of the biological function of the patient.

14. The non-transitory machine-readable storage medium of claim 13, wherein the operations further comprise transmitting the threshold to the first sensor.

15. The non-transitory machine-readable storage medium of claim 14, wherein the operations further comprise decommissioning the first sensor.

16. The non-transitory machine-readable storage medium of claim 13, wherein the operations further comprise transmitting the sensor data to the first sensor.

17. A method, comprising:
receiving, by a system comprising a processor, a communication from a first sensor adapted to be removably coupled to a skin surface of a patient;
determining that the first sensor is replacing a second sensor currently removably coupled to the skin surface of the patient by:
determining, based on the communication from the first sensor, an identifier of the first sensor;
identifying the patient;
retrieving a record associated with the patient; and
determining that the identifier of the first sensor is omitted from the record associated with the patient;
based on determining that the first sensor is replacing the second sensor:
obtaining, by the system, historical sensor data of the patient;
determining, by the system, a normative vital sign of the patient according to the historical sensor data;
accessing, by the system in an information storage system, a protocol related to at least one of an illness experienced by the patient or a therapy administered to the patient;
determining, by the system, a threshold according to the normative vital sign and the protocol; and
transmitting, by the system to the first sensor, the threshold,
wherein the threshold is different than a normative threshold applicable to a general population.

18. The method of claim 17, wherein the historical sensor data comprises a collection of health examinations performed on the patient over a period of time.

19. The method of claim 17, wherein the normative vital sign comprises at least one of a pulse rate, a temperature, a respiration rate, a blood pressure, a measure of oxygenated arterial blood, an electrocardiogram profile, or a measure of perspiration.

* * * * *